(12) United States Patent
Tin

(10) Patent No.: US 9,325,966 B2
(45) Date of Patent: Apr. 26, 2016

(54) DEPTH MEASUREMENT USING MULTISPECTRAL BINARY CODED PROJECTION AND MULTISPECTRAL IMAGE CAPTURE

(71) Applicant: CANON KABUSHIKI KAISHA, Tokyo (JP)

(72) Inventor: Siu-Kei Tin, Milpitas, CA (US)

(73) Assignee: CANON KABUSHIKI KAISHA, Tokyo (JP)

(*) Notice: Subject to any disclaimer, the term of this patent is extended or adjusted under 35 U.S.C. 154(b) by 418 days.

(21) Appl. No.: 13/839,292

(22) Filed: Mar. 15, 2013

(65) Prior Publication Data

US 2014/0028800 A1 Jan. 30, 2014

Related U.S. Application Data

(60) Provisional application No. 61/677,382, filed on Jul. 30, 2012, provisional application No. 61/759,083, filed on Jan. 31, 2013.

(51) Int. Cl.
| | | |
|---|---|---|
| H04N 13/02 | (2006.01) | |
| G01N 21/55 | (2014.01) | |
| G01B 11/25 | (2006.01) | |
| G01N 21/31 | (2006.01) | |
| G01N 21/49 | (2006.01) | |

(52) U.S. Cl.
CPC ........ *H04N 13/0203* (2013.01); *G01B 11/2509* (2013.01); *G01B 11/2513* (2013.01); *G01N 21/31* (2013.01); *G01N 21/49* (2013.01); *G01N 21/55* (2013.01); *H04N 13/0253* (2013.01)

(58) Field of Classification Search
CPC .......... H04N 13/0203; H04N 13/0253; G01B 11/2509; G01B 11/2513; G01N 21/31; G01N 21/49; G01N 21/55
See application file for complete search history.

(56) References Cited

U.S. PATENT DOCUMENTS

| | | | | |
|---|---|---|---|---|
| 5,253,302 A | * | 10/1993 | Massen | 382/110 |
| 5,815,286 A | * | 9/1998 | Matsuba et al. | 358/3.19 |
| 6,587,701 B1 | * | 7/2003 | Stranc et al. | 600/310 |
| 6,937,348 B2 | | 8/2005 | Geng | 356/603 |
| 7,039,228 B1 | * | 5/2006 | Pattikonda et al. | 382/145 |
| 7,113,651 B2 | | 9/2006 | Liang | 382/284 |
| 7,349,104 B2 | | 3/2008 | Geng | 356/603 |

(Continued)

FOREIGN PATENT DOCUMENTS

WO 2011/054083 5/2011

OTHER PUBLICATIONS

Geng, Jason, "Rainbow Three-Dimensional Camera: New Concept of High-Speed Three-Dimensional Vision Systems", Opt. Eng. 35(2), 376-383 (Feb. 1, 1996).

(Continued)

*Primary Examiner* — Jay Patel
*Assistant Examiner* — Joseph Su
(74) *Attorney, Agent, or Firm* — Fitzpatrick, Cella, Harper & Scinto

(57) ABSTRACT

Illumination of an object with spectral structured light, and spectral measurement of light reflected therefrom, for purposes which include derivation of a three-dimensional (3D) measurement of the object, such as depth and/or contours of the object, and/or for purposes which include measurement of a material property of the object, such as by differentiating between different types of materials.

52 Claims, 17 Drawing Sheets

(56) References Cited

U.S. PATENT DOCUMENTS

| | | | |
|---|---|---|---|
| 7,463,349 B1 | 12/2008 | Biellak et al. | 356/237.2 |
| 7,826,047 B2 | 11/2010 | Shibata et al. | 356/237.2 |
| 8,208,141 B2* | 6/2012 | Schmidt et al. | 356/402 |
| 8,224,064 B1* | 7/2012 | Hassebrook et al. | 382/154 |
| 8,224,425 B2 | 7/2012 | Freeman et al. | 600/473 |
| 8,243,286 B2 | 8/2012 | Palme et al. | 356/604 |
| 8,284,279 B2 | 10/2012 | Park et al. | 348/266 |
| 8,982,184 B2* | 3/2015 | Damera-Venkata et al. | 348/43 |
| 2002/0071034 A1* | 6/2002 | Ito et al. | 348/152 |
| 2002/0196415 A1* | 12/2002 | Shiratani | 353/31 |
| 2003/0078479 A1* | 4/2003 | Hall et al. | 600/310 |
| 2003/0090729 A1* | 5/2003 | Loce et al. | 358/3.06 |
| 2004/0151369 A1* | 8/2004 | Schwotzer | 382/154 |
| 2005/0077860 A1* | 4/2005 | Hagen | 318/629 |
| 2005/0207645 A1* | 9/2005 | Nishimura et al. | 382/170 |
| 2005/0237359 A1* | 10/2005 | Yoshida | 347/43 |
| 2007/0071285 A1* | 3/2007 | Kontsevich | 382/103 |
| 2007/0115484 A1* | 5/2007 | Huang et al. | 356/604 |
| 2007/0285554 A1* | 12/2007 | Givon | 348/340 |
| 2010/0157047 A1* | 6/2010 | Larkin et al. | 348/135 |
| 2011/0050859 A1* | 3/2011 | Kimmel et al. | 348/50 |
| 2012/0033064 A1* | 2/2012 | Yamada et al. | 348/79 |
| 2012/0033099 A1* | 2/2012 | Zaraga et al. | 348/223.1 |
| 2012/0229606 A1* | 9/2012 | Rodrigue et al. | 348/46 |
| 2012/0277559 A1* | 11/2012 | Kohl-Bareis et al. | 600/324 |

OTHER PUBLICATIONS

Geng, Jason, "Structured-Light 3D Surface Imaging: A Tutorial," Advances in Optics and Photonics, vol. 3, Issue 2, pp. 128-160 (2011).

Gühring, Jens, "Dense 3-D Surface Acquisition by Structured Light Using Off-The-Shelf Components", Institute for Photogrammetry, University of Stuttgart, Germany.

Gupta, M., Agrawal, A., Veeraraghavan, A. and Narasimhan, S., Structured Light 3D Scanning in the Presence of Global Illumination, CVPR 2011.

Gupta, Mohit, et al., "A Practical Approach to 3D Scanning in the Presence of Interreflections, Subsurface Scattering and Defocus".

Kim, Harvey, Kittle, Rushmeier, Dorsey, Prum and Brady, 3D Imaging Spectroscopy for Measuring Hyperspectral Patterns on Solid Objects, SIGGRAPH 2012.

Manabe, Y., Parkkinen, J., Jaaskelainen, T. and Chihara, K., Three Dimensional Measurement Using Color Structured Patterns and Imaging Spectrograph, ICPR 2002.

Pages, Jordi, et al., "Overview of Coded Light Projection Techniques for Automatic 3D Profiling", Institut d'Informatica i Aplicacions, Universitat de Girona, Robotics and Automation, 2003, Proceedings ICRA '03, vol. 1, pp. 133-138 (2003).

Wust, Clarence, et al., "Surface Profile Measurement Using Color Fringe Projection", Machine Vision and Applications, vol. 4, pp. 193-203 (1991).

Zhang L., B. Curless, and S.M. Seitz, "Rapid Shape Acquisition Using Color Structured Light and Multi-pass Dynamic Programming," In Proceedings of the 1st International Symposium on 3D Data Processing, Visualization, and Transmission (3DPVT), Padova, Italy, Jun. 19-21, 2002, pp. 24-36.

Zhang L. et al., "Projection Defocus Analysis for Scene Capture and Image Display", Association for Computing Machinery, Inc., pp. 907-915 (2006).

U.S. Appl. No. 13/839,457, filed Mar. 15, 2013, Inventor: Siu-Kei Tin.

* cited by examiner

DEPTH MEASUREMENT USING MULTISPECTRAL BINARY CODED PROJECTION AND MULTISPECTRAL IMAGE CAPTURE

CROSS-REFERENCE TO RELATED APPLICATIONS

This application claims the benefit of U.S. Provisional Patent Application No. 61/677,382, filed Jul. 30, 2012, and U.S. Provisional Patent Application No. 61/759,083, filed Jan. 31, 2013, the contents of both of which are hereby incorporated by reference as if fully stated herein.

FIELD

The present disclosure relates to illumination of an object with structured light, and measurement of light reflected therefrom, for purposes which include derivation of a three-dimensional (3D) measurement of the object, such as depth and/or contours of the object.

BACKGROUND

In the field of 3D scanning using structured light, it has been considered to use binary coded patterns, which are black and white patterns. See, for example, Gupta et al., 2011. In addition, it has also been considered to use "rainbow projections", which are color coded patterns. See, for example, U.S. Pat. No. 7,349,104 to Geng. Manabe et al. combine 3 bit planes of Gray code to form a color pattern using an RGB projector.

REFERENCES

Gupta, M., Agrawal, A., Veeraraghavan, A. and Narasimhan, S., Structured light 3D scanning in the presence of global illumination, CVPR 2011.
U.S. Pat. No. 7,349,104 Geng, System and a method for three-dimensional imaging systems
Manabe, Y., Parkkinen, J., Jaaskelainen, T. and Chihara, K., Three Dimensional Measurement using Color Structured Patterns and Imaging Spectrograph, ICPR 2002.
Kim, Harvey, Kittle, Rushmeier, Dorsey, Prum and Brady, 3D Imaging Spectroscopy for Measuring Hyperspectral Patterns on Solid Objects, SIGGRAPH 2012.

SUMMARY

Binary coded patterns are robust to depth discontinuities, but multiple patterns are required. For example, to project Gray codes in 10 bits (10-bit depth resolution), a minimum of 10 projected patterns are required. This makes high-speed 3D scanning of dynamic scenes difficult. Combining 3-bit planes into one color pattern using the 3 channels of an RGB projector can reduce the number of projected patterns, but due to the crosstalk between the channels of a broadband RGB projector, a hyperspectral camera with narrow band sensitivity must be used in some systems. Hyperspectral imaging requires a long capture time for each scene and is not suitable for real-time capture of dynamic scenes or when fast sorting is desired.

Conventional spectroscopy is capable only of single point measurements. Imaging spectroscopy, such as described by Kim, et al., 2012, combines 3D measurement techniques and hyperspectral imaging, but requires a long capture time, making it unsuitable for real-time classification of materials.

Other color coded patterns, such as the rainbow projections, are spatial coding. They assume that depth does not change abruptly across the object. In other words, they are not robust to depth discontinuities.

In a first aspect described herein, an object is illuminated with structured light that is also spectrally structured, and light reflected therefrom is measured spectrally, for purposes which include derivation of a three-dimensional (3D) measurement of the object, such as depth and/or contours of the object.

In a second aspect described herein, an object is illuminated with structured light that is also spectrally structured, and light reflected therefrom is measured spectrally, for purposes which include measurement of a material property of the object, such as by differentiating between different types of materials. As one simple example, there is a differentiation between an object whose material is plastic and an object whose material is rubber.

In a third aspect described herein, an object is illuminated with structured light that is also spectrally structured, and light reflected therefrom is measured spectrally, for purposes which include derivation of a three-dimensional (3D) measurement of the object, such as depth and/or contours of the object. The 3D measurement is used to calculate a reflectance property, such as by using calculations of a surface normal vector of the object from the 3D measurement, and estimating the reflectance property from the 3D measurement, surface normal vector and spectral measurements of reflected light, for purposes which include measurement of a material property of the object, such as by differentiating between different types of materials.

As used in this description, the terms "multichannel projector" and "multi-primary projector" are generally equivalent to each other and may be used interchangeably. Likewise, as used in this description, the terms "spectral structured light" and "multispectral coded projection" should generally be considered equivalent to each other and may be used interchangeably, with the term "multispectral binary coded projection" being a special case.

In a somewhat more detailed summary of at least the first aspect, and at least partly of the second and third aspects, in some embodiments, a method of measuring depth of a scene using a multichannel projector with relatively-narrow spectrally-banded channels at predetermined wavelengths and a multispectral camera with relatively-broad spectrally-banded channels, wherein the spectral sensitivities of the camera channels at the wavelengths of the projector channels form a well-conditioned matrix, comprises projecting a multispectral binary pattern onto the scene, wherein the multispectral binary pattern is composed of binary images, one for each channel of the projector; capturing one or more images of the scene with the multispectral camera; and recovering the depth of the scene by analyzing the captured one or more images.

In some embodiments of the method, the number of projector channels is more than 3 and the number of camera channels is at least the number of projector channels. In some embodiments, the number of projector channels is 10, each channel of the projector is monochromatic, each channel of the projector is associated with a monochromatic laser source, or each channel of the projector is associated with a monochromatic LED light source.

Also, in some embodiments of the method, the spectral sensitivity of each channel of the multispectral camera responds to at most one wavelength of a channel of the projector; a binary image is designated for projection in a projector channel by a rule that minimizes error; the binary images for the channels of the projector are ranked according to a significance value, and a binary image with a higher significance value is designated for a projector channel with a wavelength at which camera spectral sensitivity is higher; or information about the spectral reflectance in the scene is available, and a binary image with higher significance value is designated for a projector with a wavelength at which a combination of camera spectral sensitivity and spectral reflectance is higher.

Furthermore, in some embodiments, analyzing the captured image includes converting the multispectral image into multiple binary images, one for each projector channel; the conversion is performed by comparing each channel of an image based on the multispectral image with a channel-dependent threshold value; the channel-dependent threshold value is also pixel-location dependent and is derived from a second multispectral image captured with an inverse multispectral binary pattern; or the image based on the multispectral image is a multispectral radiance image.

Additionally, in some embodiments, the wavelengths of the monochromatic channels are chosen to correspond to the wavelengths where the spectrum of the ambient light has low intensities, recovering the depth of the scene is performed by triangulation, or the triangulation includes determining a plane corresponding to a column of projector pixels and a line corresponding to a camera pixel and includes calculation of an intersection between the plane and the line.

The above-described systems and methods enjoy the same robustness to depth discontinuities as binary coded patterns, such as Gray code, while avoiding an unduly excessive number of projected patterns. Under the right circumstances, one-shot depth capture is theoretically possible, for example via thresholding in each channel of the multispectral camera.

In addition, some of the embodiments employ multispectral cameras (relatively broadband) instead of hyperspectral cameras (relatively narrow band). This is advantageous because multispectral imaging does not require high spectral resolution like hyperspectral imaging does and because acquisition time is much shorter, allowing real-time capture of dynamic scenes.

In a somewhat more detailed summary of at least the second and third aspects, and at least partly of the first aspect, structured light techniques are extended in scope and concept to "spectral structured light" that enables real-time determination of spectral reflectance, in some cases by capturing as few as two (2) multispectral images using a multi-primary projector and a multispectral camera. If the 3D position and surface normal vector of a scene point are known or can be derived, the spectral reflectance can be recovered from the radiance of the scene point, which in turn can be measured by a multispectral camera. 3D position of a scene point can ordinarily be obtained readily, such as through triangulation techniques. The surface normal vector of a scene point can ordinarily be obtained by applying techniques of the first aspect described above. In some embodiments of the spectral structured light system, 10-bit Gray code patterns are used as in conventional structured light, but the bit plane images are projected simultaneously using separate channels of the 10-channel projector with monochromatic primary in each channel. In some embodiments, only 2 multispectral images are captured by the multispectral camera, corresponding to the 10-bit Gray code and its inverse (complementary) code.

In some embodiments, this process of determining 3D position is applied to a collection of scene points. The collection of determined 3D positions is referred to as a 3D map. The collection of scene points may be determined by a pre-processing step applied to the multispectral images captured by the multispectral camera, such as a step of segmentation. For example, the step of segmentation may determine scene points that belong to a same material.

In some embodiments, the surface normal map is not determined based on the 3D map. Instead, a photometric stereo method is used to determine the surface normal vectors directly, wherein one or more projectors or illumination sources may be used.

In some embodiments, a method of estimating a material property of a scene by projecting one or more patterns onto the scene using a projector and capturing one or more images of the scene using a camera comprises determining 3D positions of a collection of scene points from the one or more captured images, determining surface normal vectors of the scene points in the collection of scene points from the one or more captured images, calculating a local reflectance value for each of the scene points in the collection of scene points, and fitting a global reflectance model to the local reflectance values so as to obtain an estimate of a material property parameter.

In some embodiments, the projector is a multi-primary projector with multiple channels, the camera is a multispectral camera with at least as many channels as the number of projector channels, and the one or more patterns are patterns that are composed of binary patterns in each projector channel. Also, in some embodiments, the binary patterns are based on the Gray code; the one or more patterns consist of two patterns such that for each projector channel, the composing binary pattern in one pattern is complementary to the composing binary pattern in the other pattern; or determining the 3D position of a scene point from the collection of scene points includes determining a projector-pixel coordinate and a camera-pixel coordinate corresponding to the scene point, followed by a triangulation calculation.

In some embodiments, determining the projector pixel coordinate includes recovering a binary representation of a code with each binary digit corresponding to a projector channel, recovering a binary representation of a code comprises comparing the values of the complementary binary patterns at the scene point, determining surface normal vectors comprises applying a spatial smoothing operation to the determined 3D positions in a moving window followed by fitting a tangent plane in the moving window, or determining surface normal vectors is based on a photometric stereo algorithm.

In some embodiments, calculating a local reflectance value for each of the scene points is based on the 3D position and surface normal vector of the scene point, as well as the values of the one or more captured images at a pixel corresponding to the scene point; the global reflectance model to be fitted is a constant reflectance value to be determined; or the global reflectance model to be fitted is a BRDF model ("bidirectional reflectance distribution function").

Contrary to conventional spectroscopy or imaging spectroscopy, these systems and methods enable real-time determination of material properties by capturing very few multispectral images, such as only one multispectral image or only two multispectral images or three or more multispectral images.

Some embodiments may be implemented as a method or methods according to any of the disclosure herein. Some embodiments may be implemented as an apparatus or apparatuses according to any of the disclosure herein. Representative embodiments of such apparatus may be implemented as one or more processors constructed to execute stored process steps together with memory which stores the process steps described herein for execution by the processor(s). Other representative embodiments of such apparatus may be implemented as units constructed to execute processes described herein, with such units, for example, being implemented by computer hardware in combination with software which when executed by the computer hardware causes the computer hardware to execute such processes. Some further embodiments may be implemented as non-transitory computer-readable storage media which retrievably stores computer-executable process steps which when executed by a computer cause the computer to execute such process steps.

This brief summary has been provided so that the nature of this disclosure may be understood quickly. A more complete understanding can be obtained by reference to the following detailed description and to the attached drawings.

DETAILED DESCRIPTION

Figure 1:
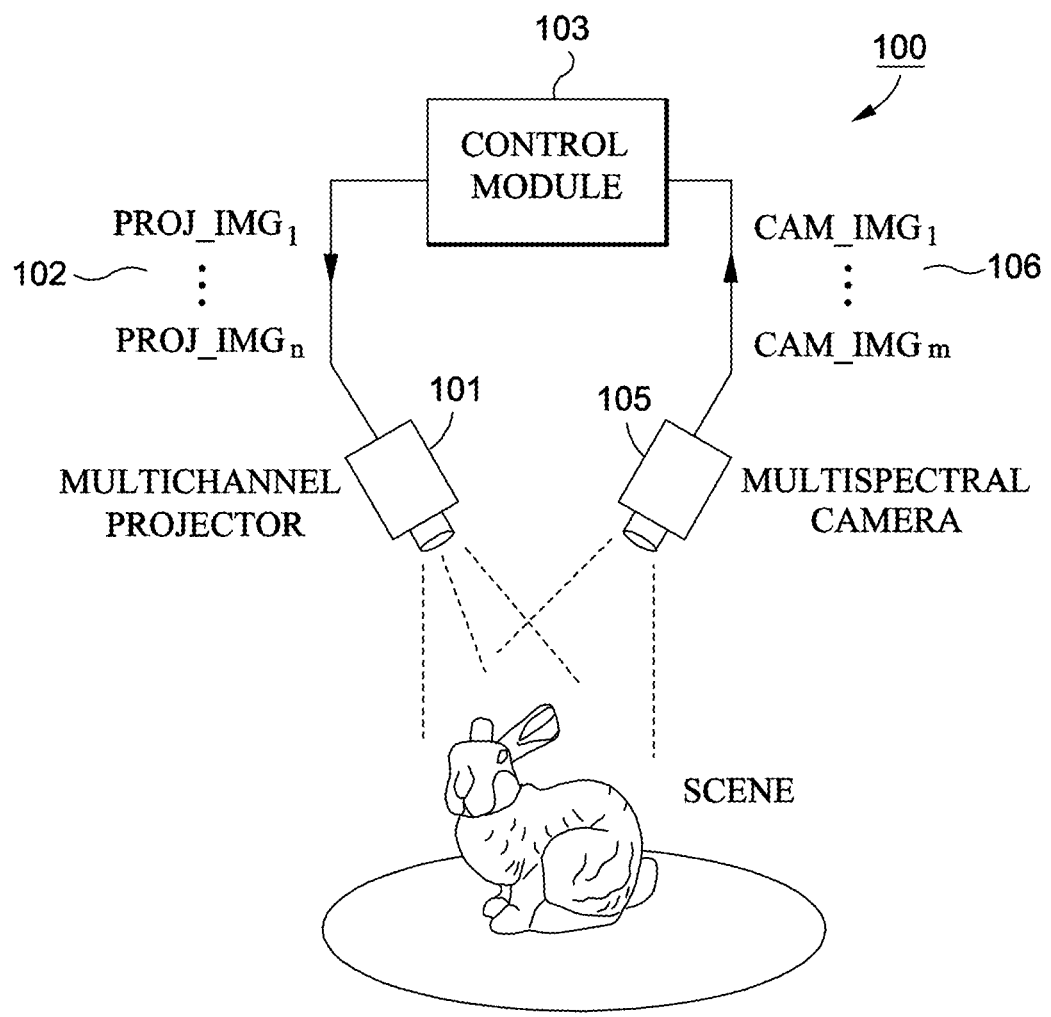
FIG. 1 is a view showing a multichannel projector for projecting spectral structured light on an object and a multispectral camera for multispectral capture of light reflected therefrom.

An example embodiment of a multispectral binary coded projection system 100 is shown in FIG. 1.

The multichannel projector 101 has n channels capable of accepting n binary images 102 such as binary images PROJ_IMG$_1$, PROJ_IMG$_2$, . . . , PROJ_IMG$_n$. The binary images are generated by a control module 103 and transmitted to the multichannel projector 101. At the same time, a multispectral camera 105 with m channels is also controlled by the control module 103 to capture an image having multiple channels, such as camera images CAM_IMG$_1$, CAM_IMG$_2$, . . . , CAM_IMG$_m$ shown at reference numeral 106, with the captured image being captured synchronously with the projected image. In one embodiment, n=m=10, and the pixel width of both the projector and the camera is at least 1024 (=$2^{10}$).

Figure 2:
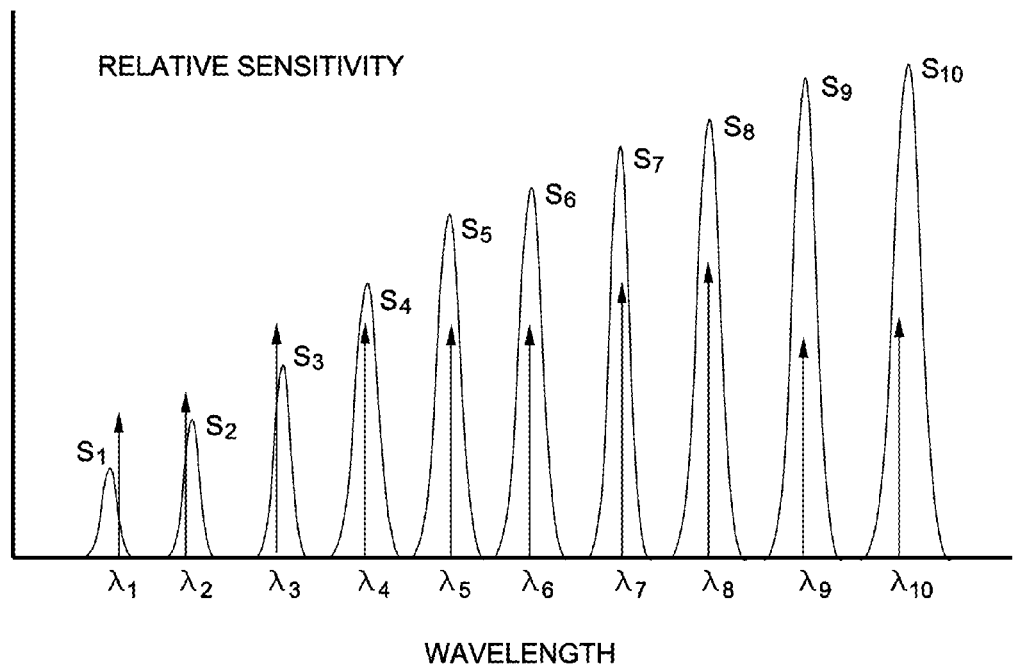
FIGS. 2 and 2A are views showing the relation between relative sensitivity of the multispectral camera as compared to the wavelengths of light projected by the multichannel projector.
Figure 2A:
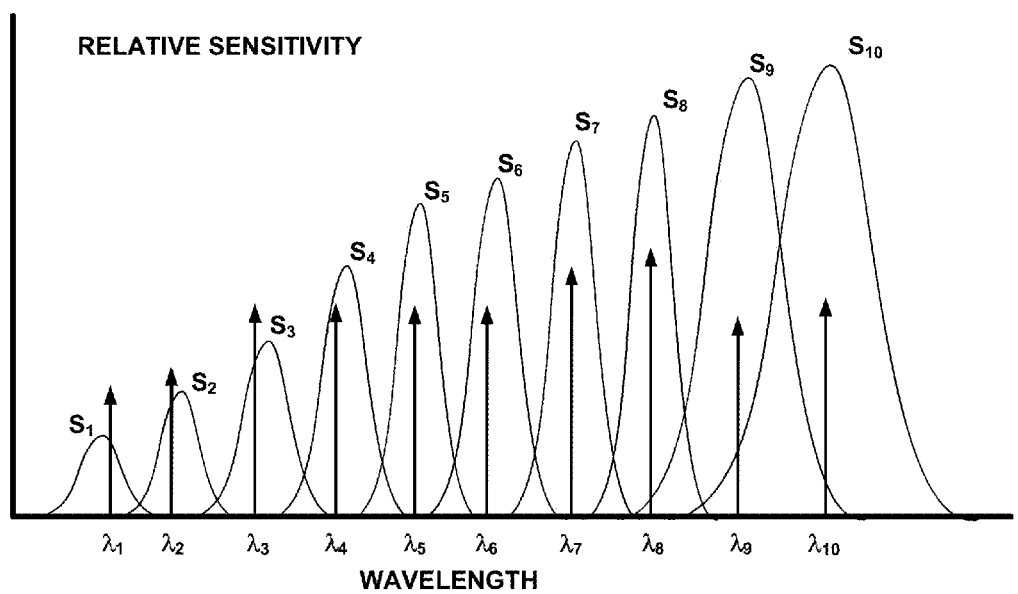

In some embodiments, each of the channels of the projector 101 is monochromatic or narrow band with a characteristic peak wavelength, e.g., $\lambda_1, \lambda_2, \ldots, \lambda_n$. In an example embodiment, the spectral sensitivity of each channel of the multispectral camera 105 responds to at most one wavelength of a channel of the projector. An example is shown in FIG. 2, where the spectral sensitivities of the camera channels are denoted $S_1(\lambda), S_2(\lambda), \ldots, S_m(\lambda)$. The figure illustrates that it is not strictly necessary for peak sensitivity of a camera channel to match exactly at the corresponding projector wavelength. However, if the peak sensitivity does occur at the projector wavelength, an (defined below) tends to be larger, resulting in a camera sensitivity matrix that is more well-conditioned, i.e., a camera sensitivity matrix that has a smaller condition number as described below. In addition, although FIG. 2 shows spectral sensitivities that are narrow banded, the spectral sensitivities are not required to be narrow banded. FIG. 2A shows spectral sensitivities that have broadband sensitivity.

In general, a camera sensitivity matrix $\Sigma = (\sigma_{ij})$ i=1, . . . , m; j=1, . . . , n is defined as follows:

$$\sigma_{ij} = S_i(\lambda_j) \qquad \text{Equation (1)}$$

Thus, with the camera sensitivities depicted in FIG. 2, the camera sensitivity matrix $\Sigma$ corresponds to a diagonal matrix.

In some embodiments, each camera-sensitivity curve may respond to multiple wavelengths of the projector, and the matrix $\Sigma$ is band diagonal. The following Tables 1 and 2 show two examples of the matrix $\Sigma$. In the first example of the matrix $\Sigma$, denoted $\Sigma_l$, the entries of the matrix are shown in the following table:

TABLE 1

Camera sensitivity matrix $\Sigma_l$; relatively low condition number

| 0.8747 | 0.1251 | 0.0001 | 0.0000 | 0.0000 | 0.0000 | 0.0000 | 0.0000 | 0.0000 | 0.0000 |
|---|---|---|---|---|---|---|---|---|---|
| 0.0569 | 0.8661 | 0.0770 | 0.0000 | 0.0000 | 0.0000 | 0.0000 | 0.0000 | 0.0000 | 0.0000 |
| 0.0001 | 0.1200 | 0.8691 | 0.0109 | 0.0000 | 0.0000 | 0.0000 | 0.0000 | 0.0000 | 0.0000 |
| 0.0000 | 0.0000 | 0.0439 | 0.8796 | 0.0760 | 0.0005 | 0.0000 | 0.0000 | 0.0000 | 0.0000 |
| 0.0000 | 0.0000 | 0.0000 | 0.1709 | 0.7053 | 0.1238 | 0.0000 | 0.0000 | 0.0000 | 0.0000 |
| 0.0000 | 0.0000 | 0.0000 | 0.0009 | 0.1715 | 0.8109 | 0.0165 | 0.0001 | 0.0000 | 0.0000 |
| 0.0000 | 0.0000 | 0.0000 | 0.0000 | 0.0000 | 0.0155 | 0.7445 | 0.2364 | 0.0036 | 0.0000 |
| 0.0000 | 0.0000 | 0.0000 | 0.0000 | 0.0000 | 0.0001 | 0.2980 | 0.6065 | 0.0952 | 0.0001 |

TABLE 1-continued

Camera sensitivity matrix $\Sigma_1$; relatively low condition number

| 0.0000 | 0.0000 | 0.0000 | 0.0000 | 0.0000 | 0.0000 | 0.0046 | 0.1521 | 0.7856 | 0.0576 |
| 0.0000 | 0.0000 | 0.0000 | 0.0000 | 0.0000 | 0.0000 | 0.0000 | 0.0006 | 0.1096 | 0.8898 |

Notice that there is some crosstalk among the camera channels.

In another example of the matrix $\Sigma$, denoted $\Sigma_2$, the entries of the matrix are shown in the following table:

TABLE 2

Camera sensitivity matrix $\Sigma_2$; relatively high condition number

| 0.4094 | 0.3437 | 0.1860 | 0.0463 | 0.0116 | 0.0028 | 0.0001 | 0.0000 | 0.0000 | 0.0000 |
| 0.2546 | 0.3252 | 0.2616 | 0.1072 | 0.0382 | 0.0122 | 0.0009 | 0.0002 | 0.0000 | 0.0000 |
| 0.1247 | 0.2425 | 0.2898 | 0.1954 | 0.0985 | 0.0422 | 0.0052 | 0.0014 | 0.0002 | 0.0000 |
| 0.0295 | 0.1005 | 0.2035 | 0.2666 | 0.2138 | 0.1359 | 0.0335 | 0.0131 | 0.0032 | 0.0003 |
| 0.0067 | 0.0347 | 0.1045 | 0.2252 | 0.2558 | 0.2188 | 0.0912 | 0.0458 | 0.0151 | 0.0022 |
| 0.0011 | 0.0085 | 0.0380 | 0.1347 | 0.2168 | 0.2493 | 0.1756 | 0.1134 | 0.0512 | 0.0114 |
| 0.0001 | 0.0008 | 0.0058 | 0.0397 | 0.1015 | 0.1734 | 0.2457 | 0.2216 | 0.1521 | 0.0594 |
| 0.0000 | 0.0002 | 0.0018 | 0.0174 | 0.0562 | 0.1169 | 0.2350 | 0.2506 | 0.2121 | 0.1098 |
| 0.0000 | 0.0000 | 0.0003 | 0.0041 | 0.0187 | 0.0522 | 0.1774 | 0.2430 | 0.2817 | 0.2227 |
| 0.0000 | 0.0000 | 0.0000 | 0.0008 | 0.0051 | 0.0190 | 0.1092 | 0.1922 | 0.3052 | 0.3685 |

There is a considerable amount of crosstalk among the camera channels, and the matrix is almost fully populated with non-zero entries.

While a diagonal matrix or a near-diagonal matrix is not required, in order to achieve fewer 3D reconstruction errors, some embodiments include a matrix $\Sigma$ that is well-conditioned.

In some embodiments, the wavelengths of the monochromatic channels are chosen to correspond to the wavelengths where the spectrum of the ambient light has low intensities. In some embodiments, some of the wavelengths lie in the NIR (near infra-red) spectrum, where the intensities of the spectrum of the ambient light are low. In some embodiments, the projector comprises monochromatic laser sources. In some embodiments, the projector comprises monochromatic LED sources.

In some embodiments, some channels of the projector are not monochromatic, but are nevertheless narrow banded such that none of the channels overlaps in spectrum with other channels, and the spectral sensitivity of each channel of the multispectral camera responds to at most one channel of the projector.

Figure 3:
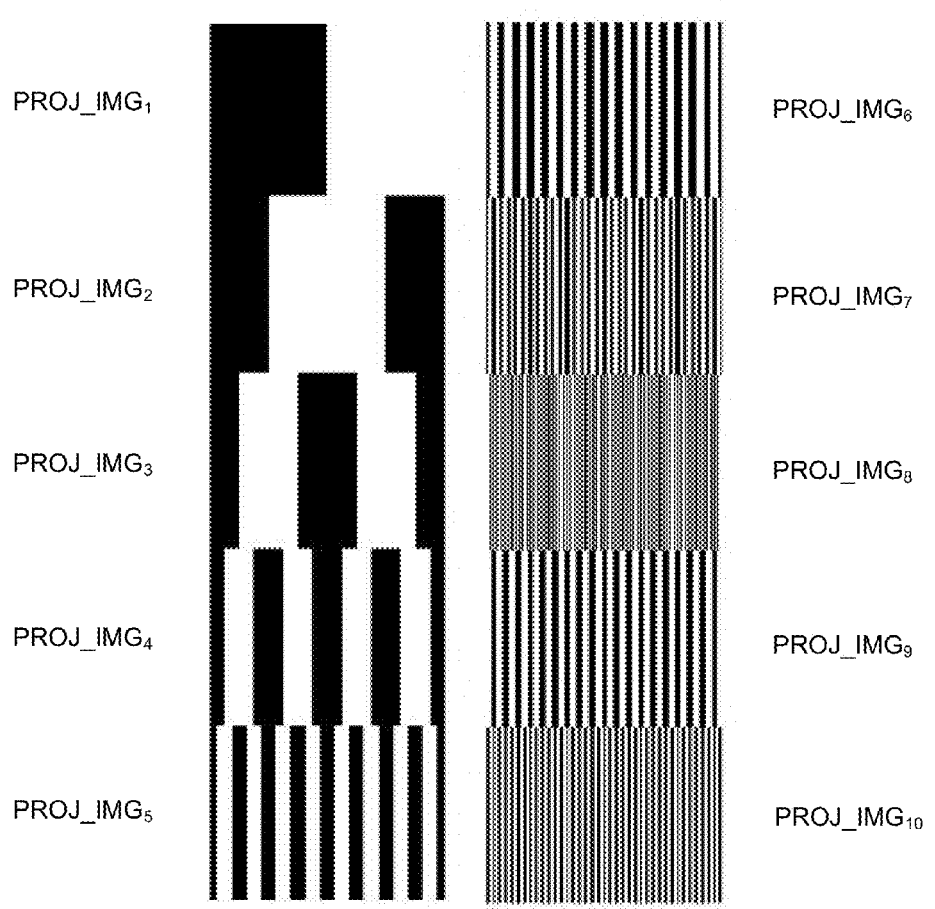
FIG. 3 is an example of input binary images based on Gray code, and shows ten (10) binary images.

In some embodiments, the input binary images 102, depicted in the FIG. 1 embodiment as $PROJ\_IMG_1$, $PROJ\_IMG_2$, ..., $PROJ\_IMG_n$, are based on Gray code. FIG. 3 shows an example of Gray code binary images for an example embodiment where n=10. Gray code is advantageous over other more naïve binary codes, such as the natural binary code, because adjacent Gray codes differ only in one bit. In the event of a recovery error for the Gray code, it is likely that the error will be limited in only one bit plane. In other words, the 3D reconstruction error tends to be lower with the Gray code.

In some embodiments, other codes are used. For example, the high frequency binary codes disclosed in Gupta, M., et al., Structured light 3D scanning in the presence of global illumination, CVPR 2011, may be used. These binary codes are related to the Gray codes via an XOR operation so that they share similar benefits of the Gray codes, while the relatively high spatial frequency of these codes provides more robustness to the adverse effect of global illumination effects such as interreflections. Other binary codes, including the natural binary codes, may be used in an embodiment where the operating environment and/or scene can be controlled so as to reduce recovery errors of the binary codes.

In conventional Gray code, it has been considered that when capturing a scene illuminated with a binary coded projection, the scene is captured by a monochrome (e.g., grayscale) camera. Analysis of the captured images then recovers the Gray code at each scene point, from which the depth map can be recovered by a technique based on triangulation.

In some embodiments described herein, a multispectral camera with m channels is used, and in addition m≥n, e.g., m=n. Each channel gives rise to a monochrome (e.g., grayscale) image similar to the conventional Gray code, but with the m channel multispectral camera of the embodiment described herein, there are m different channels captured as compared to the single channel captured with a monochrome camera. To recover the binary code associated with each scene point, it may be necessary to convert each grayscale image to a binary image. For each scene point, concatenating the binary value (e.g., 0 or 1) of each channel then gives the binary code in n bits.

In some embodiments, the operating environment is controlled (e.g., low ambient light) and the scene/objects have a known range of spectral reflectance (e.g., a lower bound of the reflectance at wavelengths $\lambda_1, \lambda_2, \ldots, \lambda_n$ can be predetermined). Given a specific grayscale captured image $CAM\_IMG_i$, taken from among the captured camera images $CAM\_IMG_1, CAM\_IMG_2, \ldots, CAM\_IMG_m$, where $1 \leq i \leq m$, a threshold value $t_i$ can be predetermined during calibration such that a binary image $BIN\_IMG_i$ can be determined by thresholding: For a pixel p, $$BIN\_IMG_i(p) = \begin{cases} 1 & \text{if } CAM\_IMG_i(p) \geq t_i \\ 0 & \text{otherwise} \end{cases} \quad \text{Equation (2)}$$

In some embodiments, radiance images are first estimated from the camera images as follows: For each pixel p, the values of radiance images $\{RAD\_IMG_i(p)\}_{i=1,2,\ldots,n}$ are obtained according to $$\begin{pmatrix} \text{RAD\_IMG}_1(p) \\ \text{RAD\_IMG}_2(p) \\ \vdots \\ \text{RAD\_IMG}_N(p) \end{pmatrix} = \frac{1}{c(p)} \cdot \Sigma^+ \begin{pmatrix} \text{CAM\_IMG}_1(p) \\ \text{CAM\_IMG}_2(p) \\ \vdots \\ \text{CAM\_IMG}_m(p) \end{pmatrix} \quad \text{Equation (3)}$$

In general, $\Sigma^+$ may be taken as the Moore-Penrose pseudo-inverse of $\Sigma$. In embodiments where m=n, $\Sigma^+ = \Sigma^{-1}$ is the usual matrix inverse. c(p) is a correction factor that depends on the pixel location p and that accounts for irradiance falloff from the optical axis of the camera. A common approximation for this factor is the "cosine $4^{th}$ power". A more precise estimate of this falloff factor can be obtained by camera calibration.

Once the radiance images are estimated, binarization can be performed by thresholding the radiance images, similar to the previous embodiment, by directly using the camera images:

$$\text{BIN\_IMG}_i(p) = \begin{cases} 1 & \text{if } \text{RAD\_IMG}_i(p) \geq t_i \\ 0 & \text{otherwise} \end{cases} \quad \text{Equation (4)}$$

In some embodiments, the thresholds $t_i$ are determined in turn by a predetermined ratio $\tau_i$:

$$t_i = \tau_i \cdot \max_p \text{RAD\_IMG}_i(p) \quad \text{Equation (5)}$$

In some embodiments, $\tau_i = 0.5$.

In these embodiments involving radiance recovery, because radiance images are estimated by inverting $\Sigma$, if $\Sigma$ is ill-conditioned (e.g., if it has a high condition number) then the quantization errors in the camera images (e.g., 16-bit integer encoding from the A/D converter in the camera image processing) may be amplified, resulting in incorrect binarized images. For example, the condition numbers of the two examples given are cond($\Sigma_1$)=2.6767 and cond($\Sigma_2$)=1.3036×$10^4$, and the depth reconstruction errors of the latter are much higher.

Figure 4:
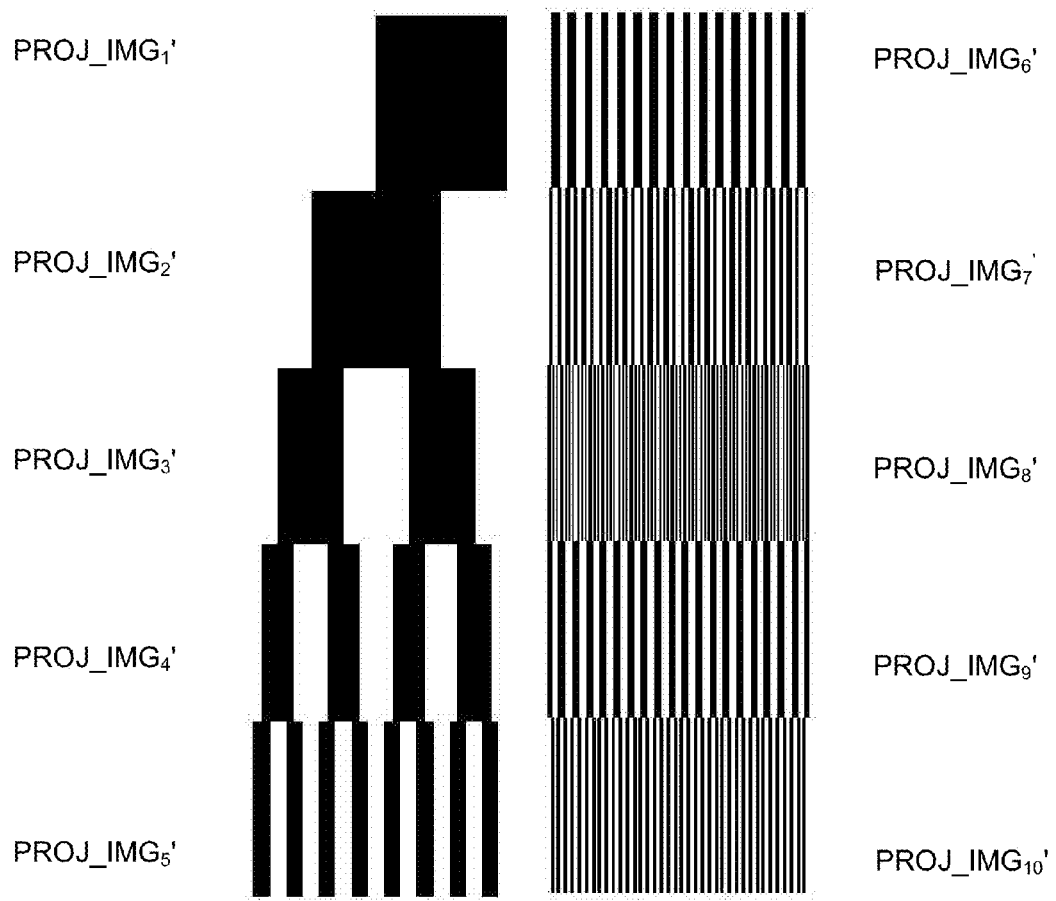
FIG. 4 shows inverse binary patterns to those of FIG. 3.

Acceptable values for the condition number are 100 and lower, more preferably 10 and lower In some embodiments, a second multispectral binary pattern is projected that is the inverse of the first multispectral binary pattern. For example, with respect to the multispectral binary pattern shown in FIG. 3, an inverse multispectral binary pattern is obtained by interchanging the values 0 and 1, as shown in FIG. 4. In other embodiments, a "null pattern", i.e., a pattern of zeroes, is projected.

Reverting to FIG. 1, the control module 103 calculates this inverse pattern and controls the multichannel projector 101 to project this pattern after projecting the first pattern. The control module 103 also controls the multispectral camera 105 to capture the scene with the inverse pattern after capturing the scene with the first pattern. The resulting multispectral image corresponds to a set of grayscale images which are denoted here as "primed" images $\text{CAM\_IMG}_1'$, $\text{CAM\_IMG}_2'$, ..., $\text{CAM\_IMG}_m'$. Given a grayscale image $\text{CAM\_IMG}_i$, where $1 \leq i \leq m$, a binary image $\text{BIN\_IMG}_i$ can be determined by comparing with $\text{CAM\_IMG}_i'$:

$$\text{BIN\_IMG}_i(p) = \begin{cases} 1 & \text{if } \text{CAM\_IMG}_i(p) > \text{CAM\_IMG}_i'(p) \\ 0 & \text{otherwise} \end{cases} \quad \text{Equation (6)}$$

In some embodiments, binarization is performed by comparing radiance images:

$$\text{BIN\_IMG}_i(p) = \begin{cases} 1 & \text{if } \text{RAD\_IMG}_i(p) > \text{RAD\_IMG}_i'(p) \\ 0 & \text{otherwise} \end{cases} \quad \text{Equation (7)}$$

The radiance images are estimated from the camera images similar to the procedure described previously.

In other embodiments, the spectral power distributions of the projector channels, $P_1(\lambda), \ldots, P_n(\lambda)$, are not monochrome or narrow band, or otherwise may have significant cross-talk with the spectral sensitivities $S_1(\lambda), \ldots, S_m(\lambda)$ of the multispectral camera. If $c=(c_1, \ldots, c_m)^T$ denotes the channels of the multispectral camera, then a channel transformation may be applied to the camera grayscale images to obtain images in a new set of virtual projector channels $q=(q_1, \ldots, q_n)^T$, where $q = \Sigma^+ c$ and $\Sigma^+$ is the Moore-Penrose pseudo-inverse of $\Sigma$, a matrix where the (i,j) entry is $$\Sigma_{ij} = \int_0^\infty S_i(\lambda) P_j(\lambda) d\lambda \quad \text{Equation (8)}$$

Then a binarization strategy similar to the ones described above is applied to the images in the virtual channels q.

In some embodiments, the converted binary images are used to determine a binary code of length n for each scene point corresponding to each pixel of the camera. In some embodiments, the recovered binary code is an n-bit Gray code, and the Gray code is further inverted to obtain a decimal index number that indicates the projector pixel column that is visible to the scene point. In other embodiments, the recovered binary code is an n-bit binary code with an associated decimal index number corresponding to a sequential or serial index of the binary code, and the decimal index number, which indicates the projector pixel column that is visible to the scene point, is recovered by an inversion process and/or a table lookup process. The depth of the scene point is then determined by a triangulation-based method.

Figure 5:
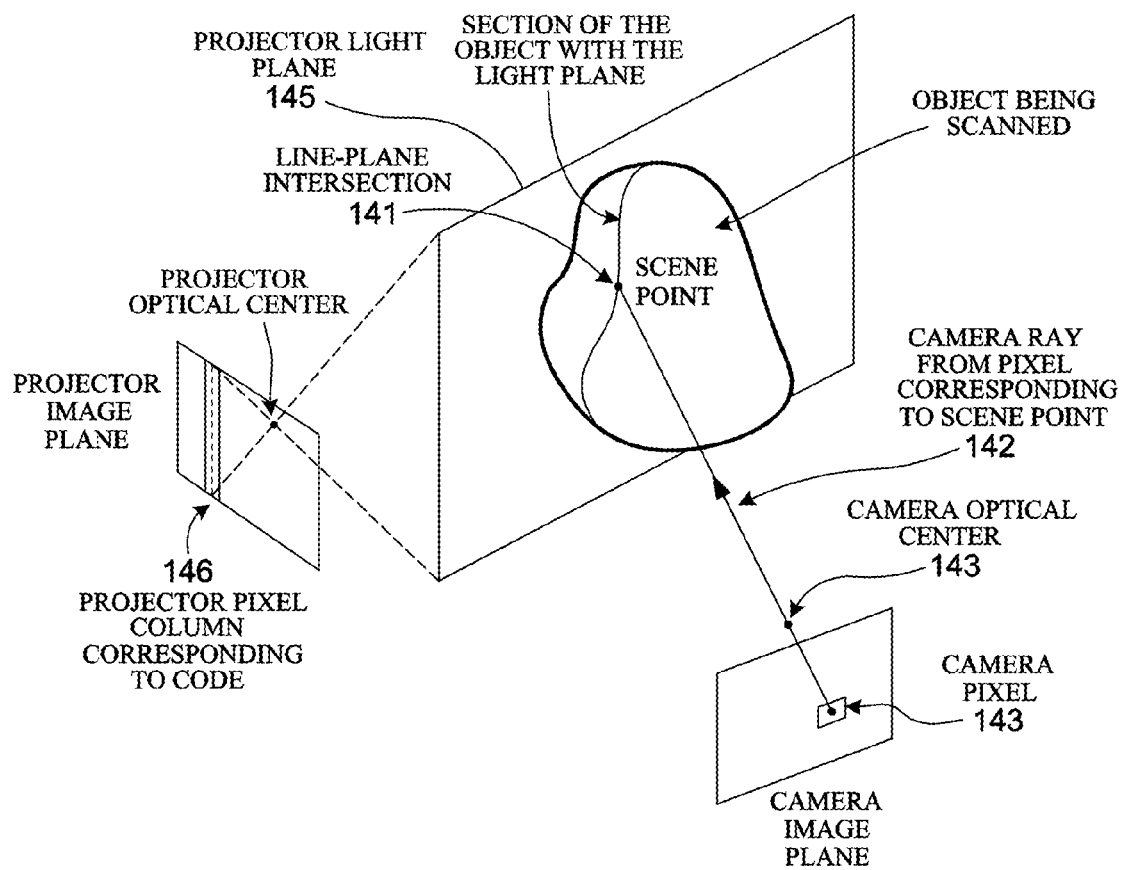
FIG. 5 is a view for explaining 3D triangulation for determining the 3D position of a scene point.

In some embodiments, the method of triangulation may be implemented based on the geometries and orientations shown in FIG. 5. As shown in FIG. 5, a method of triangulation involves a line-plane intersection 141, wherein the line corresponds to a ray 142 emanating from the camera pixel 143 in question, and the plane is a light plane 145 that corresponds to the determined projector pixel column 146. The determined intersection gives the 3D position of the scene point or, equivalently, the (projective) depth of the scene point along the camera ray.

Figure 6:
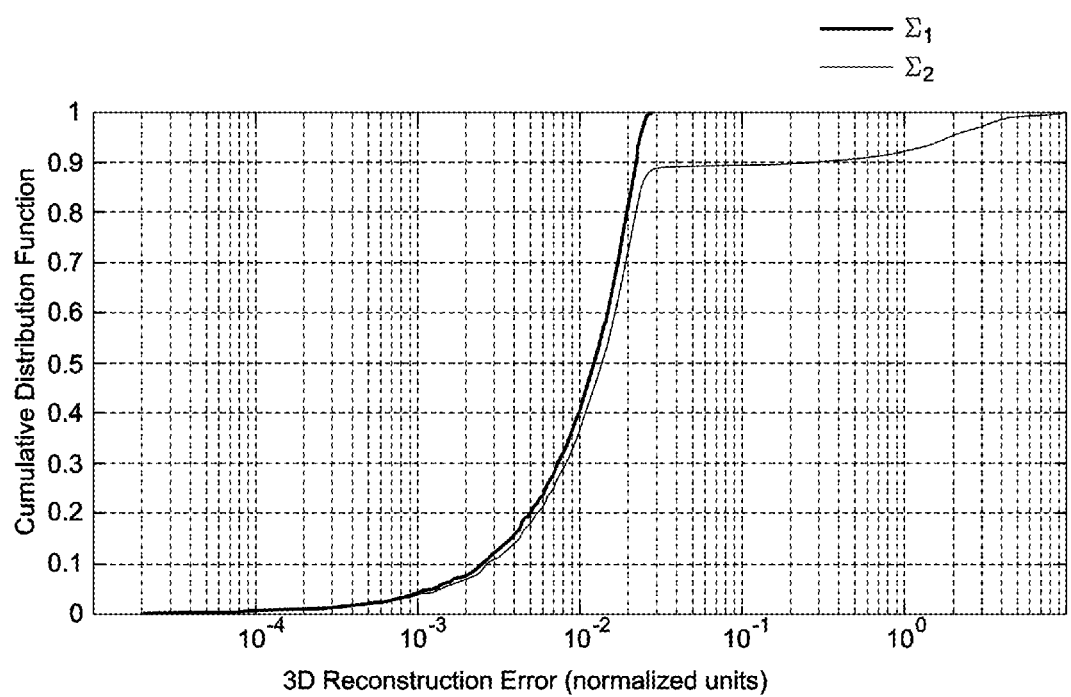
FIG. 6 shows an example of a 3D-reconstruction-error distribution for two different camera sensitivity matrices, one with a relatively low condition number and the other with a relatively high condition number.

FIG. 6 shows one example of a 3D-reconstruction-error distribution for the two camera sensitivity matrices $\Sigma_1$ and $\Sigma_2$ given in Tables 1 and 2 above. It shows that high condition numbers result in high reconstruction errors.

In some embodiments, selection of which binary pattern to project in which projector channel is based on a rule that minimizes error. In some embodiments, the selection of which binary pattern to project in which projector channel depends on a combination of the camera spectral sensitivity and the target material reflectance. In some embodiments, the projector channels have narrow band characteristic wavelengths $\lambda_1, \lambda_2, \ldots, \lambda_n$. The camera sensitivities may be such that each camera channel responds to only one of the wavelengths, which, without loss of generality, can be assumed to be in the same ordering (e.g., m=n), and the matrix $\Sigma$ is a diagonal matrix, with diagonal entries $\sigma_i = S_i(\lambda_i)$. If the spectral reflectances of the target material, denoted $\rho(\lambda)$, are known, then the quantities $\kappa_i = \sigma_i \rho(\lambda_i)$, i=1, 2, ..., n. are considered. These quantities are then sorted into non-increasing order of magnitude, resulting in a permutation of indices $\pi_i$, e.g., $\kappa_{\pi_1} \geq \kappa_{\pi_2} \geq \ldots \geq \kappa_{\pi_n}$.

In some embodiments, projector channel $\pi_i$ projects binary pattern PROJ_IMG$_i$. In other words, the larger $\kappa_i$ is for a projector channel, the more significant the bit plane in the code that is projected in that channel. In embodiments where the target-material reflectance is unknown, $\rho(\lambda_i)$ is taken to 1, and $\kappa_i$ is completely determined by the camera sensitivity at that wavelength. The principle behind these embodiments is that a higher $\kappa_i$ results in lower error (smaller condition number) in that channel, and should be preferred for recovery of high-significance bits.

The following Table 3 shows the cumulative distribution function of 3D-reconstruction errors for two cases. The first case uses the above embodiment with the non-decreasing sequence of $\kappa_i$. The second case uses the reverse ordering, i.e., non-increasing sequence of $\kappa_i$. It can be seen that the reverse-ordering embodiment provides an advantage of 0.5% for lower errors. To put the results in context, 0.5% of 1 megapixel is 5,000 pixels. Furthermore, this advantage can be achieved by simply using a more optimal choice of projector channels for the patterns, without incurring any cost in terms of extra equipment or acquisition efficiency.

TABLE 3

Comparison of cumulative distribution function of 3D-reconstruction errors

| 3D Reconstruction Error x | 0.01 | 0.02 | 0.03 | 0.04 |
|---|---|---|---|---|
| CDF F(x) for non-decreasing ordering (1st case) | 40.27% | 80.54% | 99.79% | 100.00% |
| CDF F(x) for non-increasing ordering (2nd case) | 40.75% | 81.02% | 99.70% | 100.00% |

Figure 7:
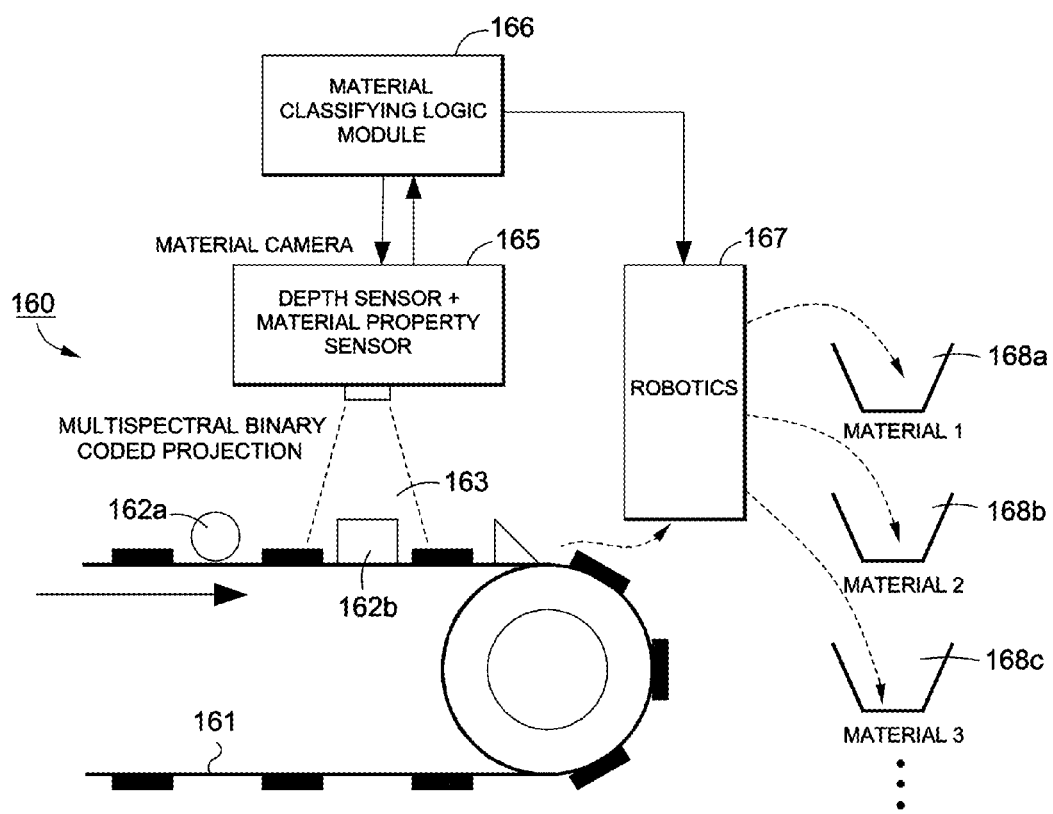
FIG. 7 shows an example embodiment of an automated sorting system such as might be used in a recycling facility, which combines 3D depth reconstruction and material classification based on projection of spectral structured light, together with material classification logic for automated sorting of objects based on material and/or based on shape.

In some embodiments, the depth sensor is incorporated into a material camera, which in turn is part of a system for classifying and sorting materials, such as in a recycling facility. FIG. 7 depicts an example arrangement.

As depicted in FIG. 7, a conveyor belt paradigm 160 provides a dynamic scene environment that requires fast capture and decision. A conveyor belt 161 transports objects 162a, 162b, etc. past an inspection station indicated generally at 163, where the object subjected to inspection is illuminated with multispectral binary coded projection by sensor 165. Sensor 165 may comprise system 100 shown in FIG. 1. Sensor 165 obtains a 3D reconstruction of the inspected object, as described above. In addition, sensor 165 determines the type of material for the inspected object, such as by distinguishing between plastic and rubber. Material classification may be based in part on spectral reflectances from the object, and it may in part rely on the 3D reconstruction from sensor 165 in order to determine expected spectral reflectances. These aspects are described in greater detail below.

Based on the determination of material type, module 166 for material classification logic activates robotics shown generally at 167, to sort the inspected objects into respective bins 168a, 168b etc.

The above-described systems and methods enjoy the same robustness to depth discontinuities as binary coded patterns, such as Gray code, while avoiding an excessive number of projected patterns. Under many ordinarily-encountered circumstances, one-shot depth capture is theoretically possible, for example via thresholding in each channel of the multispectral camera.

In addition, some of the embodiments employ multispectral cameras (relatively broadband) instead of hyperspectral cameras (relatively narrow band). This is advantageous because multispectral imaging does not require high spectral resolution like hyperspectral imaging does and because acquisition time is much shorter, allowing real-time capture of dynamic scenes.

Material classification will now be described in greater detail.

Material classification using optical methods has many practical applications, such as food inspection and recycling. One material property to measure is spectral reflectance. In this disclosure, some systems and methods extend the standard structured-light technique for three-dimensional measurement to "spectral structured light", which enables real-time determination of spectral reflectance by capturing very few multispectral images, such as only one multispectral image or only two multispectral images or three or more multispectral images, using a multi-primary projector and a multispectral camera. Some findings show the feasibility of the proposed techniques using ray-tracing simulation of multispectral images.

Conventional spectroscopy is capable only of single point measurements. Imaging spectroscopy, such as described by Kim, et al., 2012, combines 3D measurement techniques and hyperspectral imaging, but requires a long capture time, making it unsuitable for real-time classification of materials.

Structured light is known in Computer Vision for 3D measurement, such as described by Gupta et al., 2011.

In one contribution described herein, structured light techniques are extended in scope and concept to "spectral structured light" that enables real-time determination of spectral reflectance, in some cases by capturing as few as two (2) multispectral images using a multichannel projector and a multispectral camera. Simulation results, using an NVIDIA OptiX framework for a ray tracing simulation of the multispectral images, are also discussed.

For the simulation scene, some embodiments used a "V-groove" scene, which is commonly used for testing in structured light experiments. Despite its simplicity, the scene presents difficulties, such as the interreflection effect, and non-uniform illumination due to the relative position of the projector and the V-groove.

Based on a theoretical analysis of rays, if the 3D position and surface normal vector of a scene point are known or can be derived, such as with the spectral structured light arrangement described above, the spectral reflectance can be recovered from the radiance of the scene point, which in turn can be measured by a multispectral camera. In some embodiments of the spectral structured light system, 10-bit Gray code patterns are used as in conventional structured light, but the bit plane images are projected simultaneously using separate channels of the 10-channel projector with monochromatic primary in each channel. In some embodiments, only 2 multispectral images are captured by the multispectral camera, corresponding to the 10-bit Gray code and its inverse (complementary) code.

In some embodiments of the spectral structured light system, multiple grayscale patterns (i.e., not binary patterns) with predetermined phase shifts are used, and the multiple grayscale patterns are projected simultaneously by projecting each one of the multiple grayscale patterns in a corresponding one of the multiple channels of the multi-primary projector. In some embodiments, only 2 multispectral images are captured by the multispectral camera, corresponding to the multiple grayscale patterns and their inverse (complementary) patterns. For example, if a grayscale pattern is a sinusoidal pattern, then its inverse pattern is the inverted sinusoidal pattern, i.e., with a 180 degree phase difference.

In order to simulate these multispectral images, some experiments used the NVIDIA OptiX ray-tracing framework because of its flexibility to program non-standard illumination source (our multi-primary projector) and arbitrary spectral data type.

Each simulated multispectral image resulted in a stack of 10 spectral radiance images. The totality of 20 radiance images were processed analogously to the standard structured light post-processing to generate a 3D map. The 3D map was further processed to produce a surface normal map after a pre-processing (smoothing) step. The radiance images, 3D map, and surface normal map were then used to generate a stack of 10 reflectance maps. Finally, RANSAC ("RANdom SAmple Consensus") was applied to each reflectance map to find a best fit (minimum variance) reflectance value for each wavelength. The simulation obtained a spectral RMS error of 0.97% (less than 1%). In many applications, this is considered a good estimate of spectral reflectance.

Thus, using ray-tracing simulations, the tests validate the utility and versatility of a spectral structured light imaging system for fast (2-shot) determination of spectral reflectance of materials. The flexibility and extensibility of the OptiX ray tracing framework allows fast implementation of simulation of arbitrary projector-camera systems and scenes beyond conventional RGB colors. Other systems and methods may include simulations of more complex scenes and non-Lambertian materials and include determinations of other material properties, such as BRDF.

Figure 8:
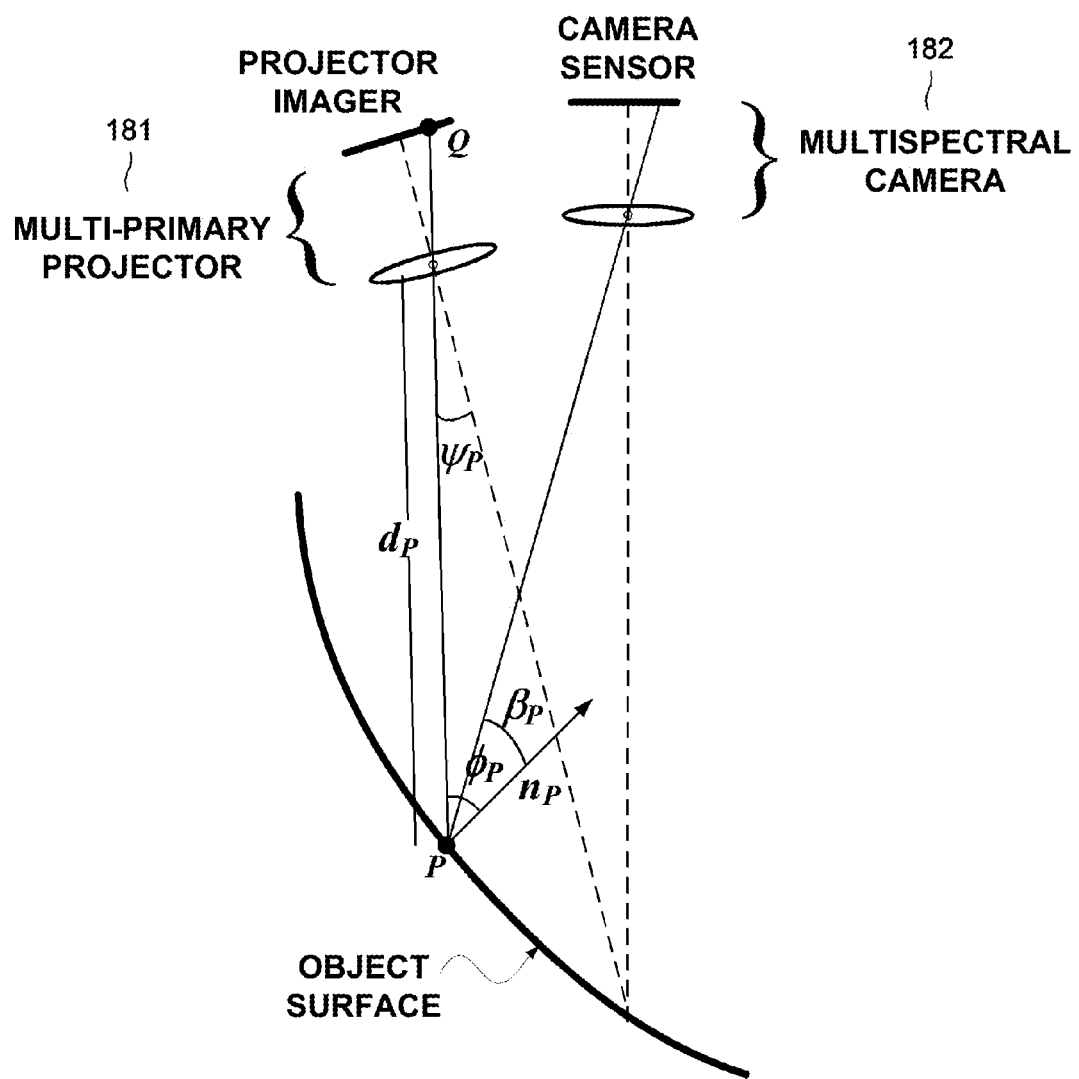
FIG. 8 is a view for explaining the 3D position of a point on the surface of an object in a scene, and for explaining the surface normal to the point.

In some embodiments, a multichannel projector 181 with N channels and a multispectral camera 182 having M channels, with M being at least N channels, are provided and geometrically calibrated in a triangulation configuration, as shown in FIG. 8. In one embodiment, N=10. In addition, each channel of the projector 181 has a monochromatic primary of wavelength $\lambda_i$, i=1, 2, . . . , N.

In FIG. 8, P is a typical scene point and $n_P$ is the surface normal vector at P. If the 3D position of P and the surface normal vector at P are known, and the projector-camera system is geometrically calibrated, then $d_P$, the distance between the scene point P and the optical center of the projector, can be determined. Similarly, the angles $\phi_P$, $\psi_P$, $\beta_P$ as indicated in FIG. 8 can also be determined, such as by geometric calibration of the projector-camera system as mentioned in the foregoing paragraph. If $v_i$ is the projector radiance (predetermined in a projector calibration, for example) in the i-th projector channel due to a projector pixel Q affecting the scene point P, and $L_i$ is the reflected radiance at P at wavelength $\lambda_i$ as recorded by the multispectral camera, then a "local reflectance value" $R(\phi_P, \beta_P, \lambda_i)$ can be determined by the following equation, provided that the i-th channel of projector pixel Q is turned on:

$$R(\phi_P, \beta_P, \lambda_i) = \frac{L_i}{v_i} \cdot \frac{d_P^2}{\cos\psi_P \cos\phi_P} \qquad \text{Equation (9)}$$

In some embodiments, Equation (9) may take on an additional multiplicative constant on the right hand side. With proper choice of units for radiance and distance, this constant may be reduced to unity. More generally, the right hand side of Equation (9) may take the form $$\frac{L_i}{v_i} \cdot \frac{F(\psi_P, d_P)}{\cos\phi_P}$$

with $F(\psi_P, d_P)$ being a function of two variables $\psi_P$ and $d_P$ dependent on a particular mathematical modeling of the projector, and with the particular instance of Equation (9) above corresponding to the special case $$F(\psi_P, d_P) = \frac{d_P^2}{\cos\psi_P} \qquad \text{Equation (9A)}$$

If the object surface is Lambertian, then another local reflectance value may also be used, $R_0(\phi_P, \beta_P, \lambda_i) = \pi R(\phi_P, \beta_P, \lambda_i)$, so that the above equation takes the following form, provided that the i-th channel of projector pixel Q is turned on:

$$R_0(\phi_P, \beta_P, \lambda_i) = \pi \frac{L_i}{v_i} \cdot \frac{d_P^2}{\cos\psi_P \cos\phi_P} \qquad \text{Equation (10)}$$

$R_0(\phi_P, \beta_P, \lambda_i)$ can be considered an approximation of the spectral reflectance $\rho(\lambda_i)$ of the Lambertian surface at wavelength $\lambda_i$.

As explained above, in order to determine the local reflectance value using one of the above equations, there is first a determination of the 3D position of P and the surface normal vector at P. The 3D position of P and the surface normal vector at P can be determined using a method of triangulation as shown in the flow diagram depicted in FIG. 9.

Figure 9:
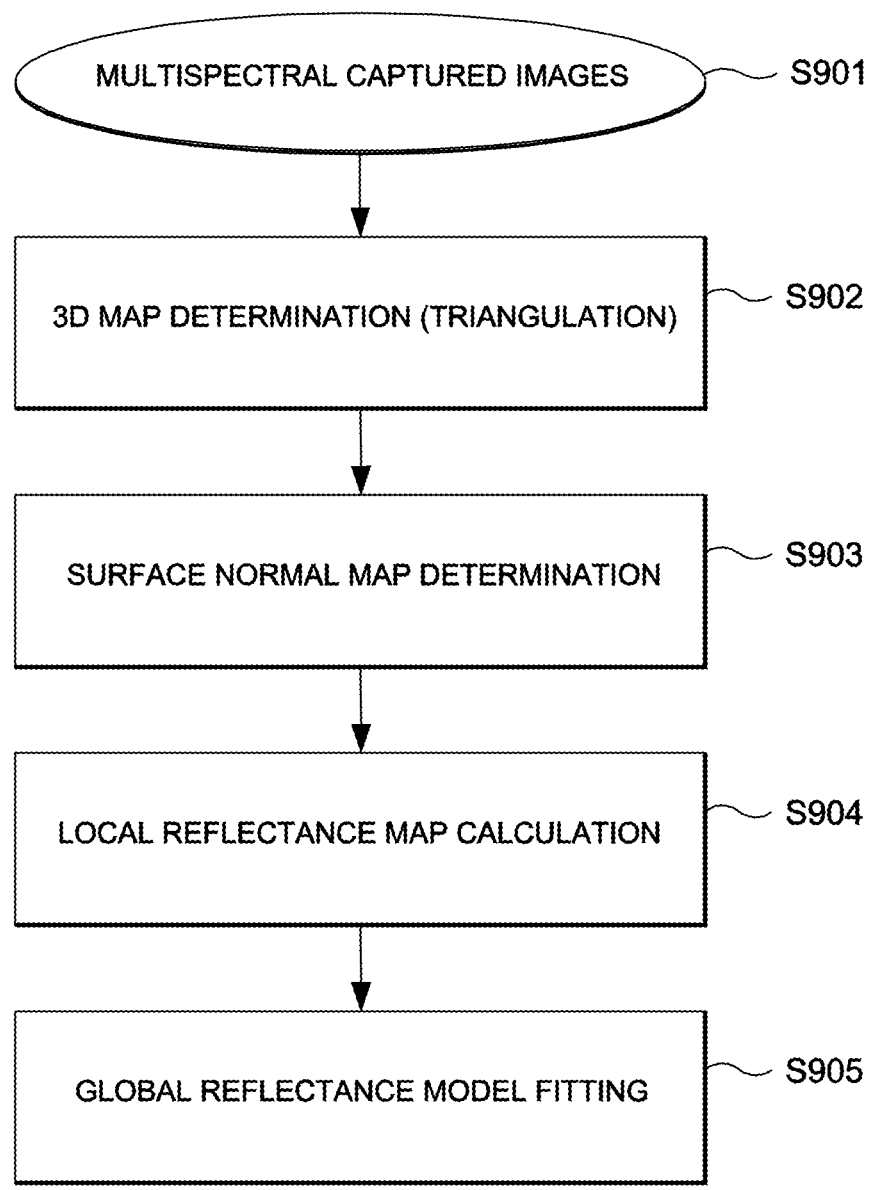
FIG. 9 is a flowchart for explaining the determination of spectral reflectance values for points in a scene, by using 3D positions of the points and by using normal vectors to the points, in order to develop a local reflectance map.

As shown in the embodiment of FIG. 9, for the 3D position, one or more patterns composed of binary patterns in each projector channel are projected onto an object in the scene. The binary patterns may be based on the Gray code or any acceptable binary code as described above. Multispectral images are captured in step S901. The 3D position of P, equivalently the depth of P, can be determined by a method of triangulation, in step S902. Furthermore, the one or more patterns may include two patterns such that for each projector channel, the composing binary pattern in one pattern is complementary, or inverse, to the composing binary pattern in the other pattern, in which case there is a corresponding multispectral capture of the complementary/inverse projections.

In some embodiments, this process of determining 3D position is applied to a collection of scene points. The collection of determined 3D positions is referred to as a 3D map, as also shown in step S902. The collection of scene points may be determined by a preprocessing step applied to the multispectral images captured by the multispectral camera, such as a step of segmentation. For example, the step of segmentation may determine scene points that belong to a same material.

A surface normal map is determined at step S903. For the surface normal vectors at the collection of scenes points, some embodiments determine the surface normal map. In some embodiments, this can be determined from the already determined 3D map. Because taking derivatives may amplify inherent noise in the 3D map, a spatial smoothing operation is applied to the determined 3D positions in a moving window of size W×W. For example, a moving averaging operation can be applied to a 3D map in an 11×11 window. After spatial smoothing, a tangent plane is fitted to the 3D positions in the W×W window, for example in the least-squares sense. The normal vector at a scene point is then taken to be a unit vector perpendicular to the fitted tangent plane.

In some embodiments, the surface normal map is not determined based on the 3D map. Instead, a photometric stereo method, perhaps using an entirely independent illumination and/or camera system, is used to determine the surface normal vectors directly, wherein one or more projectors or illumination sources may be used.

When both the 3D map and the surface normal map are determined, a local reflectance map for each wavelength $\lambda_i$ can be calculated, as shown at step S904. In the embodiment of step S904, the local reflectance map for each wavelength $\lambda_i$ is calculated based on the 3D position and surface normal vector of a scene point, as well as the values of the one or more captured images at a pixel corresponding to the scene point, as described in one of the equations (9) or (10) above.

Figure 10:
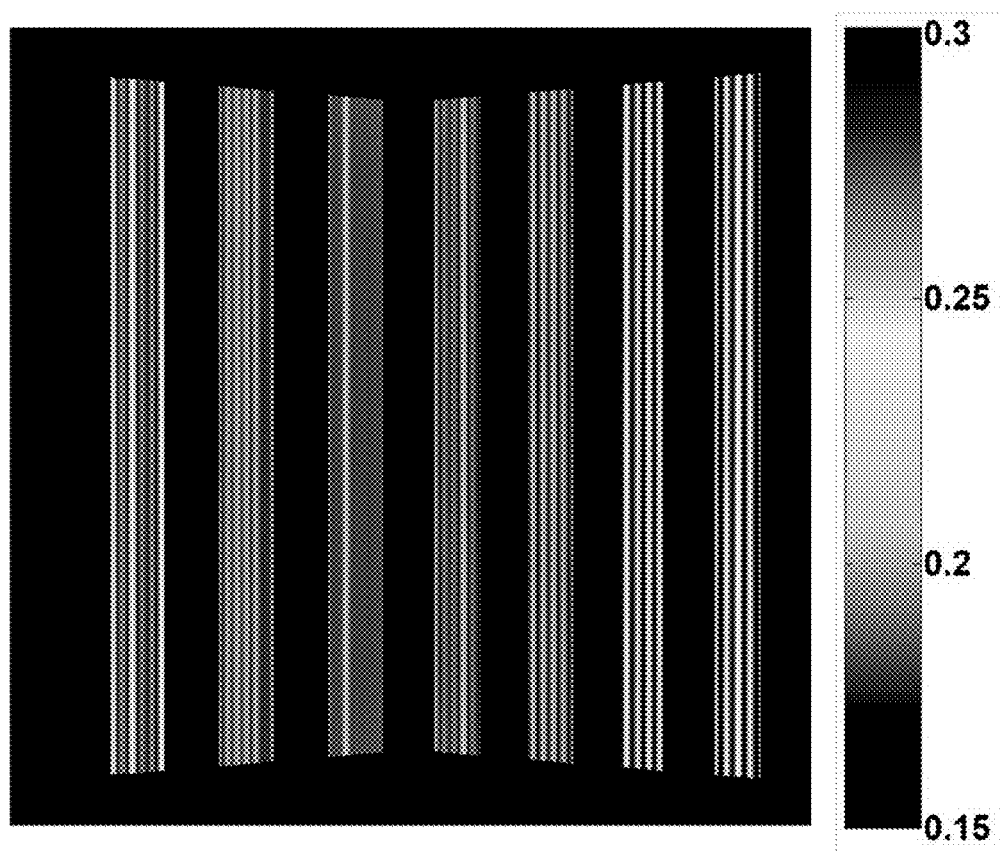
FIG. 10 is an example of a local reflectance map.

FIG. 10 shows an example of a local reflectance map for a wavelength. A scene point that is not illuminated (i.e., the corresponding projector pixel is not turned on in the channel corresponding to the wavelength) is indicated as a dark pixel. A scene point that is illuminated (i.e., the corresponding projector pixel is turned on in the channel corresponding to the wavelength) is indicated as a lit pixel with a local reflectance value calculated from Equation (10).

For a Lambertian surface with spectral reflectance $\rho(\lambda)$, a local reflectance map $R_0(\phi_P, \beta_P, \lambda_i)$ is theoretically a constant function in P, e.g., independent of $\phi_P$ and $\beta_P$. Due to illumination conditions, interreflections, or other global illumination effects, along with errors associated with finite projector and camera resolution, the local reflectance map may not be a constant even for a Lambertian surface. For example, in the illustrative example shown in FIG. 10, the local reflectance map is seen to take values ranging from 0.25 to 0.30.

Reverting to FIG. 9, a reflectance property is calculated from local reflectance values in the local reflectance map, at step S905, by fitting them to a global reflectance model. One such model is a constant global reflectance model. Another such model is an analytical BRDF (bidirectional reflectance distribution function) model, which more accurately is actually a family of models providing an abundance of analytic BRDF models. In the case of a constant global reflectance model, a reflectance property is the spectral reflectance $\rho(\lambda_i)$ at wavelength $\lambda_i$. In order to obtain the spectral reflectance $\rho(\lambda_i)$ of a Lambertian surface, a RANSAC (RANdom SAmple Consensus) algorithm may be applied to a local reflectance map to fit a constant global reflectance model. The RANSAC algorithm attempts to find a subset of pixels in the local reflectance map that are inliers. In the case of a constant global reflectance model, fitting corresponds to an averaging of the local reflectance values for the inliers, resulting in an estimate $\hat{\rho}_i$ of the true reflectance $\rho(\lambda_i)$, and the best fit is achieved by minimizing the variance or standard deviation. The RANSAC algorithm requires as input a threshold number for the least number of inliers required. In some embodiments, this threshold number of pixels is 10% of the valid pixels in the local reflectance map.

For a non-Lambertian surface, another embodiment of the global reflectance model to be fitted is an analytical BRDF (bidirectional reflectance distribution function) model. In general, such a model may take the form $f(\phi_P, \lambda_P, \lambda_i, \rho, \sigma, \ldots)$, where f is a function and $\rho, \sigma, \ldots$ are parameters of the model. For example, in the Oren-Nayar model for rough surfaces, $\rho$ is an albedo (reflectance) at $\lambda_i$, and $\sigma$ is a surface roughness parameter. Similarly, RANSAC is applied to obtain a best fit of the BRDF model for the local reflectance map R $(\phi_P, \beta_P, \lambda_i)$, resulting in estimates of the BRDF model parameters $\hat{\rho}, \hat{\sigma}, \ldots$. These parameters can then be used as material property parameters. In another example of the Cook-Torrence model for metallic surfaces, parameters such as albedo and root-mean-square slope of the surface microfacets can be used as material property parameters.

Further embodiments of a global reflectance model for a non-Lambertian surface include a BTF (bidirectional texture function) model or a BSSRDF (bidirectional surface scattering reflectance distribution function) model. Generally, it is preferred for the global reflectance model to be an analytical model with a few parameters for fitting to.

Contrary to conventional spectroscopy or imaging spectroscopy, these systems and methods enable real-time determination of material properties by capturing very few (1 or 2) multispectral images.

With specific reference to the aforementioned feature of calculating a local reflectance value for multiple ones of each of the scene points, as mentioned in connection with step S904 and which is based on the 3D position and surface normal vector of the scene point, as well as the values of the one or more captured images at a pixel corresponding to the scene point, the following may be stated.

Figure 11:
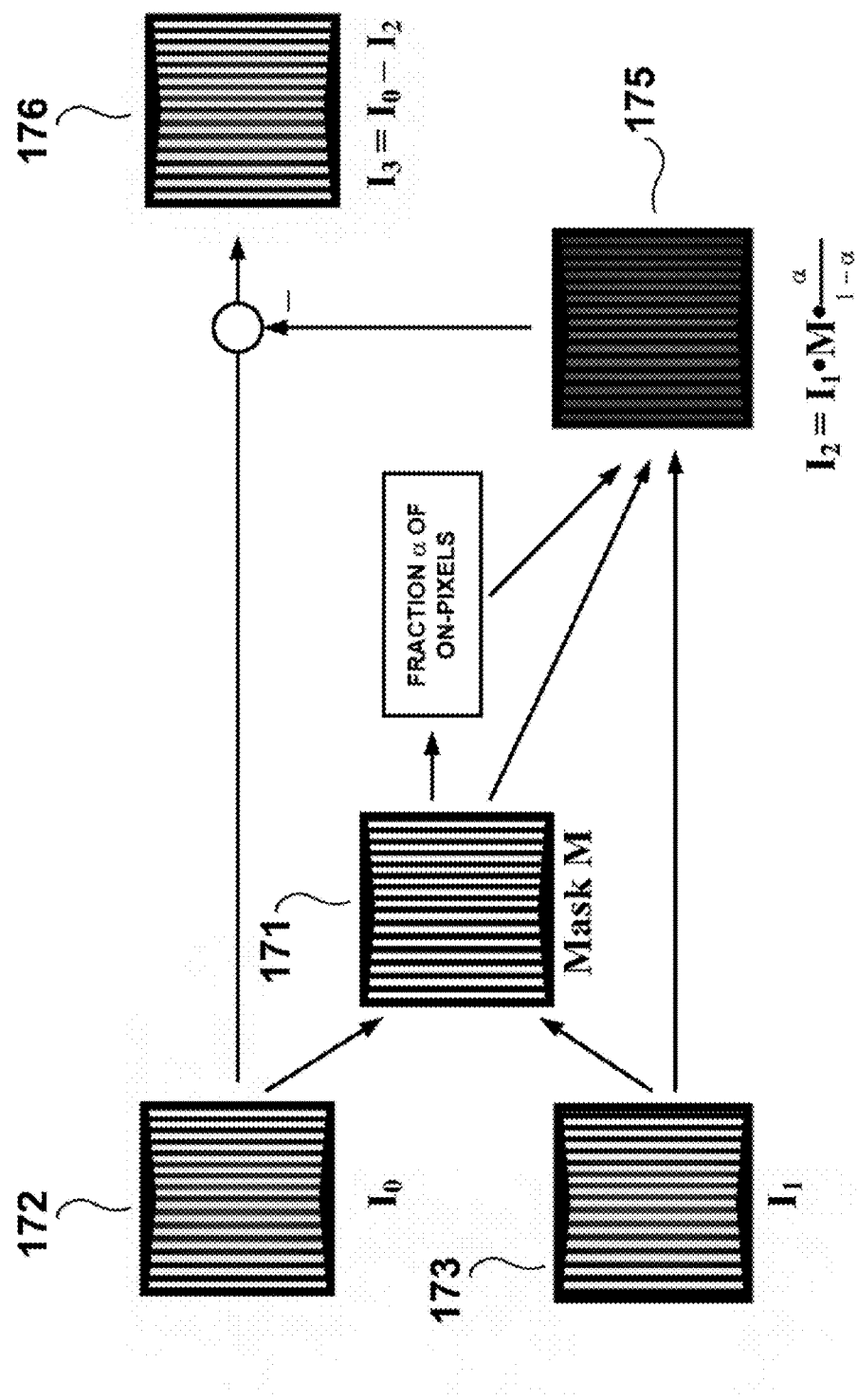
FIG. 11 is a view for explaining one example of calculating a local reflectance value, by using two or more patterns that include binary patterns in each projector channel.

In some embodiments for calculating the local reflectance value, one or more patterns that include binary patterns in each projector channel are used. In addition, the one or more patterns consist of two patterns such that, for each projector channel, the included binary pattern in one pattern is complementary to the included binary pattern in the other pattern. The following description focuses on a typical projector channel. For this channel, the multispectral camera records two radiance images $I_0$ and $I_1$ that are complementary, or inverse to each other. Even though the projected patterns are binary, the recorded images would in general have more than two values, e.g., they are grayscale images instead of binary images. FIG. 11 shows an example.

In FIG. 11, a binary mask M, shown at 171, is determined. This mask M represents pixels that are determined to correspond to projector pixels that are turned on in that channel. In an embodiment, the binary mask M is determined by performing the Boolean comparison operation $I_0 > I_1$ on the two radiance images $I_0$ (shown at 172) and $I_1$ (shown at 173).

The fraction $\alpha$ of pixels that are determined to be "on-pixels" is then determined from the binary mask M. For patterns based on the Gray code, $\alpha$ is typically approximately 0.5, although the actual value depends on the images $I_0$ and $I_1$, in the sense that $\alpha$ is calculated from M which in turn is calculated from images $I_0$ and $I_1$.

A correction image $I_2$ (shown at 175) is then determined. In FIG. 11, the correction image $I_2$ appears relatively dark and corresponds to "noise" due to interreflections. The correction image $I_2$ is determined using the following equation:

$$I_2 = I_1 \cdot M \cdot \frac{\alpha}{1 - \alpha} \qquad \text{Equation (11)}$$

Pixel-wise multiplication by the mask M may ensure that correction is applied only to the on-pixels in $I_0$. The local reflectance calculation may be done only for projector pixels that are turned on for that channel, so that correction to the on-pixels is the only concern. The reason for the need for correction may be to correct for global illumination effects such as interreflections.

Finally, a corrected radiance image $I_3$ (shown at 176) is obtained by the equation $I_3 = I_0 - I_2$. The radiance values $L_i$ at the on-pixels in $I_3$ are then used in the local reflectance calculations.

Figure 12:
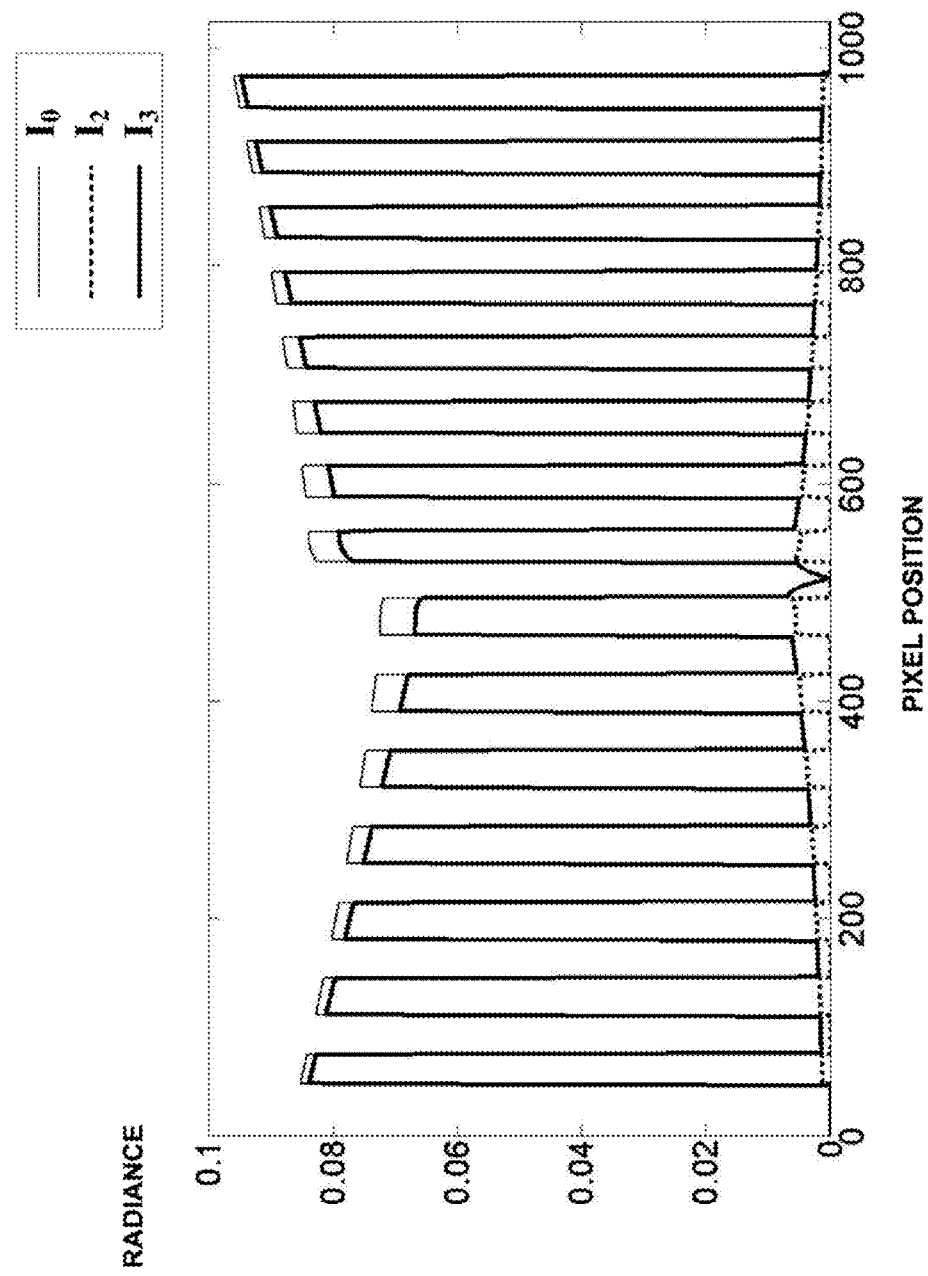
FIG. 12 shows the radiance profiles of $I_0$, $I_2$, and $I_3$ of FIG. 11, along a horizontal row of pixels.

One example of illustrative radiance profiles of $I_0$, $I_2$, and $I_3$ along a horizontal row of pixels is shown in FIG. 12.

As seen in FIG. 12, the thin continuous line represents the profile of $I_0$, while the thick dotted line and thick continuous line represent respectively the profiles of $I_2$ and $I_3$. Comparing the profile of $I_0$ at on-pixels and off-pixels, it is clear that the correction of the global component of illumination is effective.

Figure 13:
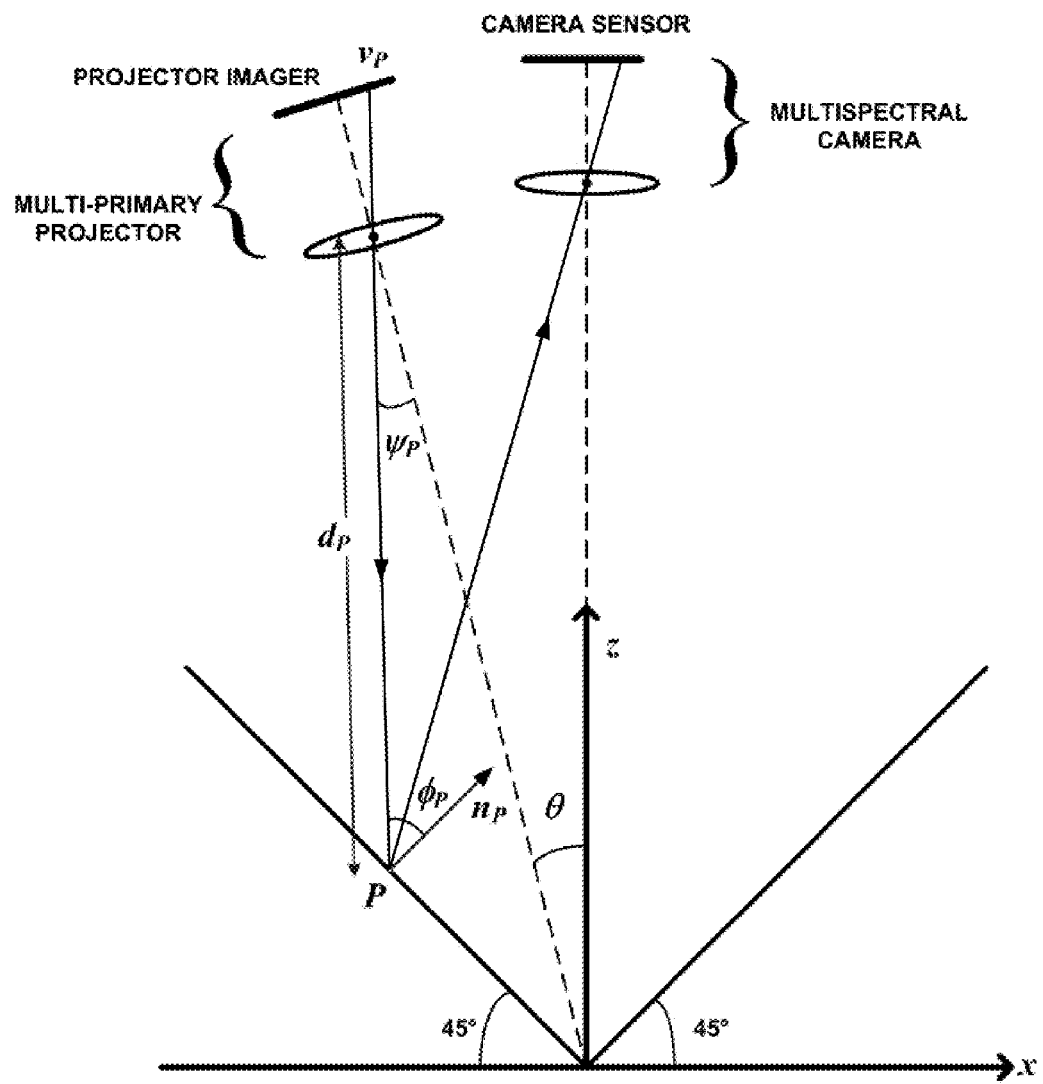
FIG. 13 is a view for explaining a geometry of a ray for a "v-groove" scene.
Figure 14:
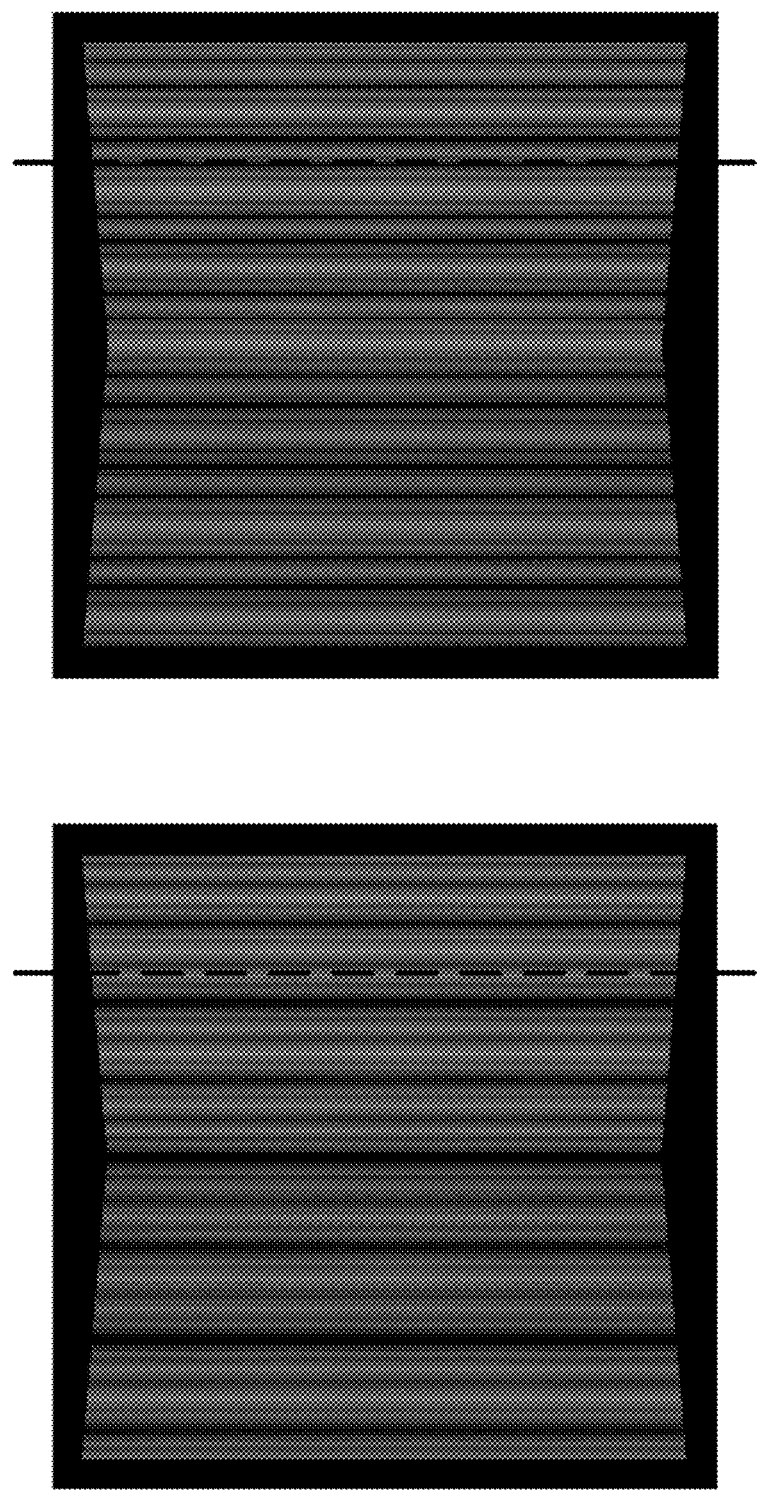
FIG. 14 is an RGB visualization of the simulation of a spectral Gray code pattern (left) and its inverse pattern (right).
Figure 15:
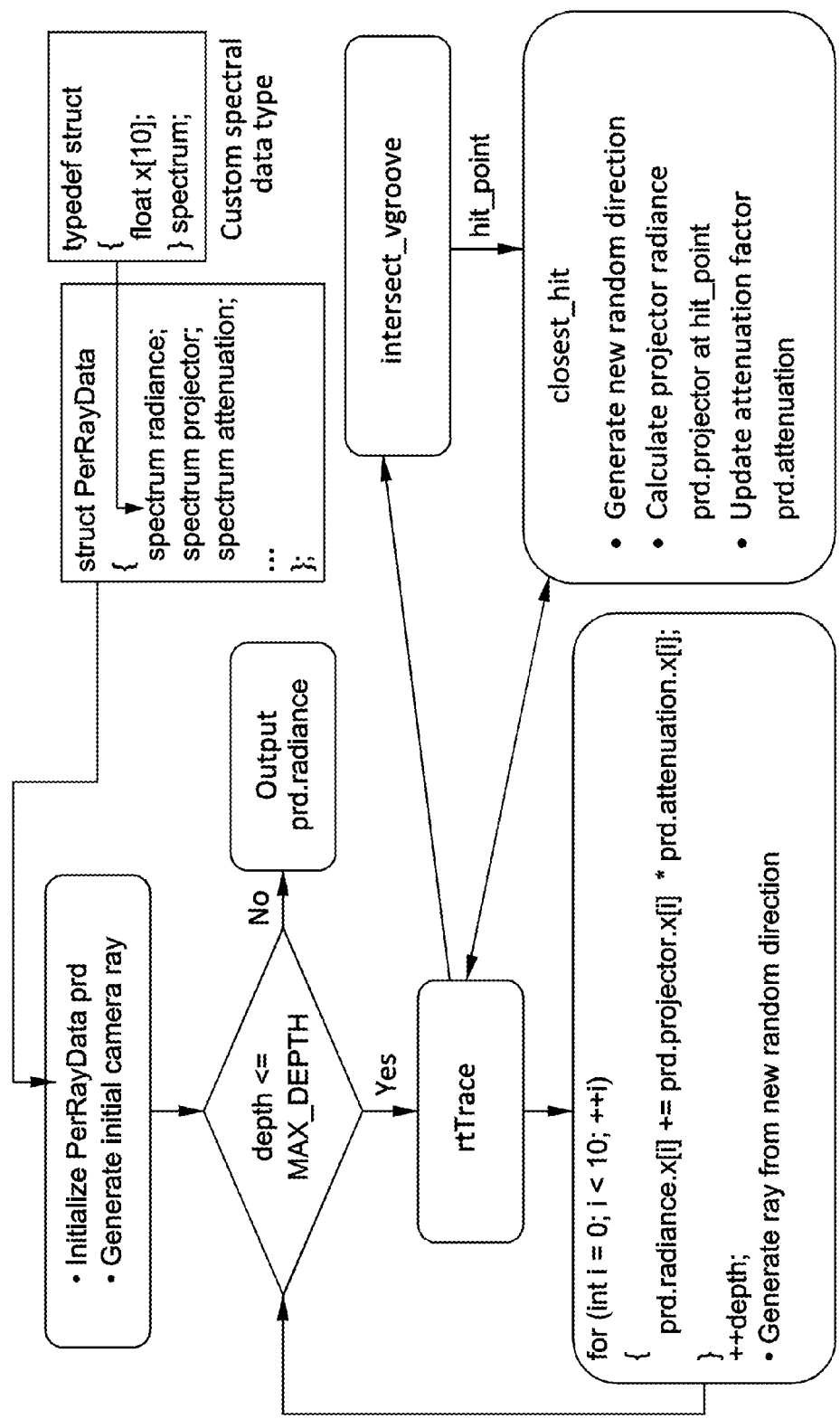
FIG. 15 is view for explaining a simulation framework.

FIGS. 13, 14 and 15 describe ray-tracing simulations that validate the utility and versatility of a spectral structured light imaging system for fast (2-shot) determination of spectral reflectance of materials, or more generally to the determination of a material property. One common material property to measure is spectral reflectance.

Consider a "V-groove" scene, which is commonly used as a test scene in structured light experiments, as mentioned by Gupta et al., 2011, as shown in FIG. 13.

This figure depicts a cross-section of a 3D Lambertian surface shown in cross-section at the X-Z plane. The equation of the Lambertian surface is $$z=|x| \text{ where } -1 \le x \le 1 \text{ and } -1 \le y \le 1 \quad \text{Equation (12)}$$

The Lambertian surface has reflectance $\rho(\lambda)$ and in this FIG. $\theta=5$ degrees.

Such a "V-groove" scene presents difficulties such as the interreflection effect, and non-uniform illumination due to the relative position of the projector and the V-groove.

Assume that the multi-primary projector has 10 monochromatic channels with wavelengths $\lambda_1, \lambda_2, \ldots, \lambda_{10}$. If the radiance values of a scene point P at these wavelengths are $L_1, L_2, \ldots, L_{10}$, as recorded by the multispectral camera, then the spectral reflectance factors at these wavelengths can be recovered by the following equation:

$$\rho(\lambda_i) \approx \pi \cdot L_i \cdot d_P^2 / \cos \psi_P \cos \phi_P, i=1,2,\ldots,10 \quad \text{Equation (13)}$$

In this equation, the approximate equality would be exact if there were no interreflections. To use this equation, both the 3D position and surface normal vector are determined at P.

FIG. 15 is view for explaining a simulation framework. In the simulation, the NVIDIA OptiX framework was used for ray tracing simulation of spectral radiance images because of its flexibility to program non-standard illumination source and arbitrary spectral data type. In addition, the flexibility and extensibility of the OptiX ray tracing framework allows fast implementation of simulation of arbitrary projector-camera systems and scenes beyond conventional RGB colors.

Some key features of the simulation are:

(a) A new data type is defined to support 10-channel spectral data.

(b) The standard path tracing algorithm is modified to work with our projector with pinhole optics: In the standard algorithm, the path ends only when it hits a light source, which would not happen with a pinhole.

(c) The radiance images are averaged over 5000+ frames to minimize random noise.

(d) 10-bit Gray code patterns are used as in conventional structured light, but the bit plane images are projected simultaneously using separate channels of the multi-primary projector. Only 2 multispectral images are captured, corresponding to the 10-bit Gray code and its inverse (complementary) code.

(e) Visualization of the multispectral radiance image is provided by real time conversion of multispectral radiance images to RGB images for display.

In more detail, as illustrated in FIG. 15, the simulation program starts by initializing an instance 'prd' of a data structure 'PerRayData', and generating an initial camera ray. The data structure 'PerRayData' is a custom data structure containing fields including 'radiance', 'projector', and 'attenuation', of a custom data type 'spectrum'. The custom data type 'spectrum' is defined as a structure containing a vector of ten components, each represented in an IEEE single precision floating point number. A program variable 'depth', initially set to one, is compared to a predetermined constant 'MAX_DEPTH' which determines a maximum number of levels of recursion in the ray tracing simulation. If the maximum number of levels of recursion is exceeded ('depth>MAX_DEPTH'), the simulation program outputs the radiance of the ray, 'prd.radiance'. If the maximum number of levels of recursion is not exceeded ('depth<=MAX_DEPTH'), ray tracing is performed by the OptiX built-in function rtTrace in order to update the data structure 'prd'. Afterwards, the current radiance 'prd.radiance' of the ray is also updated for each of the ten components, the program variable 'depth' is incremented by one, and a "continuing ray" is generated that has a new random direction calculated from a function closest_hit, which is described below. The process then goes back to the step of comparing 'depth' to the predetermined constant 'MAX_DEPTH'. In the above described process, the OptiX built-in function rtTrace interacts with two custom functions: intersect_vgroove and closest_hit. intersect_vgroove calculates the intersection point 'hit_point' of the current ray and the V-groove. The intersection point 'hit_point' is then passed into the closest_hit function, which generates a new random direction, calculates projector radiance 'prd.projector' at 'hit_point', and updates attenuation factor 'prd.attenuation', the latter two being used in the subsequent updating of the current radiance of the ray as described above.

10-bit Gray code patterns are used as in conventional structured light, but the bit plane images are projected simultaneously using separate channels of the multi-primary projector. Only 2 multispectral images are captured, corresponding to the 10-bit Gray code and its inverse (complementary) code. A grayscale illustration of an RGB visualization of OptiX simulation of spectral Gray code pattern (left) and its inverse pattern (right) are shown in FIG. 14. An example pixel column is shown on the spectral Gray code pattern (left) that is associated with an example code 1010001001, resulting in non-zero reflection spectrum in wavelengths $\lambda_1$, $\lambda_3$, $\lambda_7$ and $\lambda_{10}$. A corresponding pixel column is shown on the inverse pattern (right) that is associated with inverse code 0101110110, resulting in non-zero reflection spectrum in wavelengths $\lambda_2$, $\lambda_4$, $\lambda_5$, $\lambda_6$, $\lambda_8$ and $\lambda_9$.

Figure 16:
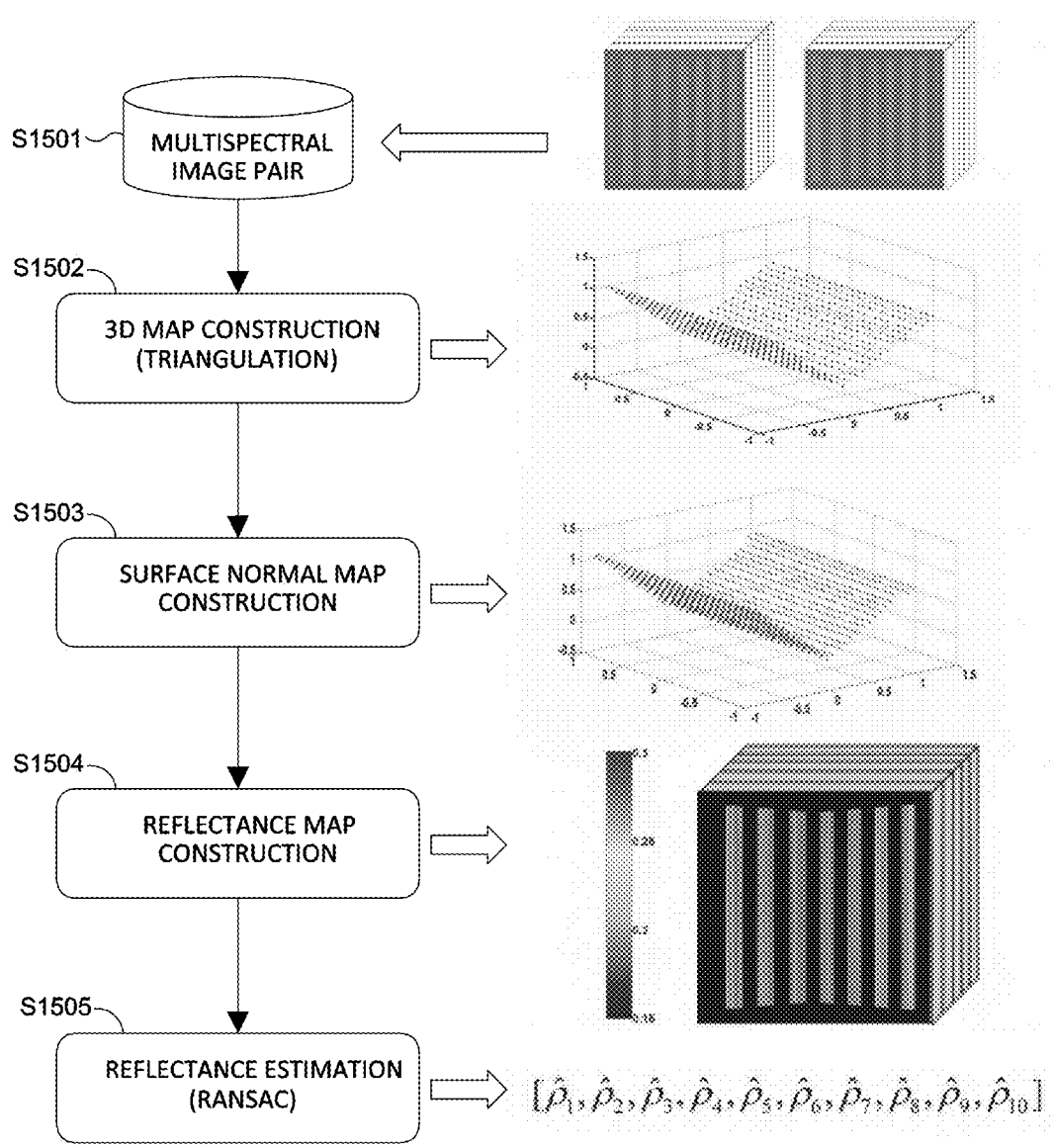
FIG. 16 is a flowchart for explaining the determination of spectral reflectance values for points in a scene, by using 3D positions of the points and by using normal vectors to the points, in order to develop a local reflectance map.

A flow diagram for one representative reconstruction algorithm is shown in FIG. 16. In a manner somewhat similar to the flow of FIG. 9, multispectral images are captured in step S1501 (here a multispectral image pair is captured), a 3D map is reconstructed in step S1502, such as by triangulation, a surface normal map is constructed in step S1503, a reflectance map is constructed in step S1504, and spectral reflectances are estimated in step S1505, such as by RANSAC analysis.

In FIG. 16, suggestive examples are provided to the right of each of the steps, so as to indicate the general nature of graphical depictions of input/output for each step.

In the simulation, each of the 2 spectral Gray code patterns results in a stack of 10 spectral radiance images.

The totality of 20 radiance images is processed analogously to structured light post-processing described above to generate a 3D map.

The 3D map is further processed to produce a surface normal map after a pre-processing (smoothing) step.

Because the 3D map and the surface normal map are now determined, the radiance images, the 3D map and the surface normal map are used to generate a stack of 10 reflectance maps by applying Equation (13) above which is reproduced here again for convenience $$\rho(\lambda_i) \approx \pi \cdot L_i \cdot d_P^2 / \cos \psi_P \cos \phi_P, i=1,2,\ldots,10 \quad \text{Equation (13), repeated}$$

Finally, RANSAC is applied to each reflectance map to find a best fit (minimum variance) reflectance value for each wavelength, yielding the results shown in the following Table 4.

TABLE 4

Comparison of ground truth reflectance of simulated Lambertian surface against estimated reflectance for each wavelength

| Wavelength (nm) | 405 | 440 | 473 | 514.5 | 543.5 | 568.2 | 611.9 | 632.8 | 659 | 694.3 |
|---|---|---|---|---|---|---|---|---|---|---|
| Ground Truth Reflectance | 0.498 | 0.606 | 0.582 | 0.412 | 0.313 | 0.268 | 0.233 | 0.240 | 0.245 | 0.225 |
| Estimated Reflectance | 0.504 | 0.616 | 0.581 | 0.426 | 0.317 | 0.277 | 0.237 | 0.250 | 0.229 | 0.215 |
| Reflectance Error (Percentage) | 0.62% | 1.02% | 0.08% | 1.46% | 0.37% | 0.93% | 0.43% | 0.98% | 1.65% | 1.02% |

The spectral RMS (root-mean-square) error can be derived from the individual spectral errors shown in Table 4. In this simulation, the spectral RMS error is 0.97% (less than 1%). In many applications, this is considered a good estimate of spectral reflectance.

Ray tracing simulations thus that validate the utility and versatility of a spectral structured light imaging system for fast (2-shot) determination of spectral reflectance of materials, or more generally to the determination of a material property.

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

The invention claimed is:

1. A method of measuring depth of a scene using a multi-channel projector with narrow spectrally banded channels each with a characteristic peak wavelength and a multispectral camera with broad spectrally banded channels, wherein the spectrums of the spectrally banded channels of the multichannel projector are narrower than the spectrums of the spectrally banded channels of the multispectral camera which are broader, wherein the spectral sensitivities of the camera channels at the characteristic peak wavelengths of the projector channels form a band diagonal matrix, the method comprising:

projecting a multispectral binary pattern onto the scene with the multichannel projector, wherein the multispectral binary pattern is composed of binary images, one for each channel of the projector;

capturing one or more images of the scene with the multispectral camera, each image being captured as a multispectral image;

converting each multispectral image into multiple binary images, one binary image for each projector channel; and recovering the depth of the scene based on the multiple binary images, one binary image for each projector channel.

2. The method according to claim 1, wherein the number of projector channels is more than 3 and the number of camera channels is at least the number of projector channels.

3. The method according to claim 2, wherein the number of projector channels is 10.

4. The method according to claim 1, wherein each channel of the projector is monochromatic.

5. The method according to claim 4, wherein each channel of the projector is associated with a monochromatic laser source.

6. The method according to claim 4, wherein each channel of the projector is associated with a monochromatic LED light source.

7. The method according to claim 4, wherein the wavelengths of the monochromatic channels are chosen to correspond to the wavelengths where the spectrum of the ambient light has low intensities.

8. The method according to claim 1, wherein the spectral sensitivity of each channel of the multispectral camera responds primarily to at most one wavelength of a channel of the projector.

9. The method according to claim 1, further comprising a ranking of the binary images relative to the channels of the projector by a rule that minimizes reconstruction error.

10. The method according to claim 1, further comprising ranking of the binary images for the channels of the projector according to significance values, and designation of a binary image with a higher significance value for a projector channel with a wavelength at which camera spectral sensitivity is higher.

11. The method according to claim 10, further comprising obtaining information about the spectral reflectance in the scene, wherein a binary image with higher significance value is designated for a projector channel with a wavelength at which a combination of camera spectral sensitivity and spectral reflectance is higher.

12. The method according to claim 1, wherein the conversion is performed by comparing each channel of an image based on the multispectral image with a channel dependent threshold value.

13. The method according to claim 12, wherein the channel dependent threshold value is also pixel location dependent and is derived from a second multispectral image captured with an inverse multispectral binary pattern.

14. The method of claim 12, wherein the image based on the multispectral image is a multispectral radiance image.

15. The method according to claim 1, wherein recovering the depth of the scene is performed by the method of triangulation.

16. The method according to claim 15, wherein the method of triangulation includes determination of a plane corresponding to a column of projector pixels and a line corresponding to a camera pixel, and calculation of an intersection between the plane and the line.

17. The method according to claim 1, wherein the band diagonal matrix has a condition number of 10 or less.

18. An apparatus for measuring depth of a scene using a multichannel projector with narrow spectrally banded channels each with a characteristic peak wavelength and a multispectral camera with broad spectrally banded channels, wherein the spectrums of the spectrally banded channels of the multichannel projector are narrower than the spectrums of the spectrally banded channels of the multispectral camera which are broader, wherein the spectral sensitivities of the camera channels at the characteristic peak wavelengths of the projector channels form a band diagonal matrix, the apparatus comprising:

one or more processors constructed to execute stored process steps; and memory which stores process steps for execution by the one or more processors;

wherein the stored process steps comprise:

projecting a multispectral binary pattern onto the scene with the multichannel projector, wherein the multispectral binary pattern is composed of binary images, one for each channel of the projector;

capturing one or more images of the scene with the multispectral camera, each image being captured as a multispectral image;

converting each multispectral image into multiple binary images, one binary image for each projector channel; and recovering the depth of the scene based on the multiple binary images, one binary image for each projector channel.

19. The apparatus according to claim 18, wherein the number of projector channels is more than 3 and the number of camera channels is at least the number of projector channels.

20. The apparatus according to claim 19, wherein the number of projector channels is 10.

21. The apparatus according to claim 18, wherein each channel of the projector is monochromatic.

22. The apparatus according to claim 21, wherein each channel of the projector is associated with a monochromatic laser source.

23. The apparatus according to claim 21, wherein each channel of the projector is associated with a monochromatic LED light source.

24. The apparatus according to claim 21, wherein the wavelengths of the monochromatic channels are chosen to correspond to the wavelengths where the spectrum of the ambient light has low intensities.

25. The apparatus according to claim 18, wherein the spectral sensitivity of each channel of the multispectral camera responds primarily to at most one wavelength of a channel of the projector.

26. The apparatus according to claim 18, wherein the stored process steps further comprise a ranking of the binary images relative to the channels of the projector by a rule that minimizes reconstruction error.

27. The apparatus according to claim 18, wherein the stored process steps further comprise ranking of the binary images for the channels of the projector according to significance values, and designation of a binary image with a higher significance value for a projector channel with a wavelength at which camera spectral sensitivity is higher.

28. The apparatus according to claim 27, wherein the stored process steps further comprise obtaining information about the spectral reflectance in the scene, wherein a binary image with higher significance value is designated for a projector channel with a wavelength at which a combination of camera spectral sensitivity and spectral reflectance is higher.

29. The apparatus according to claim 18, wherein the conversion is performed by comparing each channel of an image based on the multispectral image with a channel dependent threshold value.

30. The apparatus according to claim 29, wherein the channel dependent threshold value is also pixel location dependent and is derived from a second multispectral image captured with an inverse multispectral binary pattern.

31. The apparatus of claim 29, wherein the image based on the multispectral image is a multispectral radiance image.

32. The apparatus according to claim 18, wherein recovering the depth of the scene is performed by the method of triangulation.

33. The apparatus according to claim 32, wherein the method of triangulation includes determination of a plane corresponding to a column of projector pixels and a line corresponding to a camera pixel, and calculation of an intersection between the plane and the line.

34. The apparatus according to claim 18, wherein the band diagonal matrix has a condition number of 10 or less.

35. An apparatus for measuring depth of a scene using a multichannel projector with narrow spectrally banded channels each with a characteristic peak wavelength and a multispectral camera with broad spectrally banded channels, wherein the spectrums of the spectrally banded channels of the multichannel projector are narrower than the spectrums of the spectrally banded channels of the multispectral camera which are broader, wherein the spectral sensitivities of the camera channels at the characteristic peak wavelengths of the projector channels form a band diagonal matrix, the apparatus comprising:
   a projecting unit constructed to project a multispectral binary pattern onto the scene with the multichannel projector, wherein the multispectral binary pattern is composed of binary images, one for each channel of the projector;
   a capturing unit constructed to capture one or more images of the scene with the multispectral camera, each image being captured as a multispectral image;
   a converting unit constructed to convert each multispectral image into multiple binary images, one binary image for each projector channel; and
   a recovering unit constructed to recover the depth of the scene based on the multiple binary images, one binary image for each projector channel.

36. The apparatus according to claim 35, wherein the number of projector channels is more than 3 and the number of camera channels is at least the number of projector channels.

37. The apparatus according to claim 36, wherein the number of projector channels is 10.

38. The apparatus according to claim 35, wherein each channel of the projector is monochromatic.

39. The apparatus according to claim 38, wherein each channel of the projector is associated with a monochromatic laser source.

40. The apparatus according to claim 38, wherein each channel of the projector is associated with a monochromatic LED light source.

41. The apparatus according to claim 38, wherein the wavelengths of the monochromatic channels are chosen to correspond to the wavelengths where the spectrum of the ambient light has low intensities.

42. The apparatus according to claim 35, wherein the spectral sensitivity of each channel of the multispectral camera responds primarily to at most one wavelength of a channel of the projector.

43. The apparatus according to claim 35, further comprising a ranking unit constructed to rank the binary images relative to the channels of the projector by a rule that minimizes reconstruction error.

44. The apparatus according to claim 35, further comprising a ranking unit constructed to rank the binary images for the channels of the projector according to significance values, and a designation unit constructed to designate a binary image with a higher significance value for a projector channel with a wavelength at which camera spectral sensitivity is higher.

45. The apparatus according to claim 44, further comprising an obtaining unit constructed to obtain information about the spectral reflectance in the scene, wherein a binary image with higher significance value is designated for a projector channel with a wavelength at which a combination of camera spectral sensitivity and spectral reflectance is higher.

46. The apparatus according to claim 35, wherein the conversion is performed by comparing each channel of an image based on the multispectral image with a channel dependent threshold value.

47. The apparatus according to claim 46, wherein the channel dependent threshold value is also pixel location dependent and is derived from a second multispectral image captured with an inverse multispectral binary pattern.

48. The apparatus of claim 46, wherein the image based on the multispectral image is a multispectral radiance image.

49. The apparatus according to claim 35, wherein recovering the depth of the scene is performed by the method of triangulation.

50. The apparatus according to claim 49, wherein the method of triangulation includes determination of a plane corresponding to a column of projector pixels and a line corresponding to a camera pixel, and calculation of an intersection between the plane and the line.

51. The apparatus according to claim 35, wherein the band diagonal matrix has a condition number of 10 or less.

52. A non-transitory computer-readable storage medium which retrievably stores computer-executable process steps which when executed by a computer cause the computer to execute a method of measuring depth of a scene using a multichannel projector with narrow spectrally banded channels each with a characteristic peak wavelength and a multispectral camera with broad spectrally banded channels, wherein the spectrums of the spectrally banded channels of the multichannel projector are narrower than the spectrums of the spectrally banded channels of the multispectral camera which are broader, wherein the spectral sensitivities of the camera channels at the characteristic peak wavelengths of the projector channels form a band diagonal matrix, the method comprising:
   projecting a multispectral binary pattern onto the scene with the multichannel projector, wherein the multispectral binary pattern is composed of binary images, one for each channel of the projector;
   capturing one or more images of the scene with the multispectral camera, each image being captured as a multispectral image;

converting each multispectral image into multiple binary images, one binary image for each projector channel; and recovering the depth of the scene based on the multiple binary images, one binary image for each projector channel.

* * * * *